United States Patent
Klimasauskas et al.

(10) Patent No.: US 9,988,673 B2
(45) Date of Patent: *Jun. 5, 2018

(54) NUCLEIC ACID PRODUCTION AND SEQUENCE ANALYSIS

(71) Applicant: Vilnius University, Vilnius (LT)

(72) Inventors: Saulius Klimasauskas, Vilnius (LT); Zdislav Stasevskij, Vilnius (LT); Edita Kriukiene, Vilnius (LT)

(73) Assignee: VILNIUS UNIVERSITY, Vilnius (LT)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/072,677

(22) Filed: Mar. 17, 2016

(65) Prior Publication Data

US 2017/0016055 A1    Jan. 19, 2017

Related U.S. Application Data

(63) Continuation of application No. 13/679,538, filed on Nov. 16, 2012, now Pat. No. 9,347,093.

(30) Foreign Application Priority Data

Nov. 17, 2011  (GB) ................................ 1119903.1

(51) Int. Cl.
*C12Q 1/68*     (2018.01)
*C12P 19/34*    (2006.01)

(52) U.S. Cl.
CPC ............ *C12Q 1/6853* (2013.01); *C12P 19/34* (2013.01); *C12Q 1/6846* (2013.01); *C12Q 1/6869* (2013.01); *C12Q 1/6876* (2013.01)

(58) Field of Classification Search
None
See application file for complete search history.

(56) References Cited

U.S. PATENT DOCUMENTS

| | | | |
|---|---|---|---|
| 7,465,544 B2 | 12/2008 | Rajski et al. | |
| 8,008,007 B2 | 8/2011 | Weinhold et al. | |
| 2005/0202490 A1 | 9/2005 | Makarov et al. | |
| 2007/0161007 A1 | 7/2007 | Rajski et al. | |
| 2008/0064043 A1 | 3/2008 | Berlin et al. | |
| 2009/0048427 A1* | 2/2009 | Hedgpeth | C07D 207/34 530/322 |

FOREIGN PATENT DOCUMENTS

| | | |
|---|---|---|
| EP | 1102781 | 12/2003 |
| EP | 1756313 | 2/2007 |
| EP | 1874790 | 8/2010 |
| WO | 2000/006587 | 2/2000 |
| WO | 2001/057248 | 8/2001 |
| WO | 2005/121361 | 12/2005 |
| WO | 2006/091628 | 8/2006 |
| WO | 2006/108678 | 10/2006 |
| WO | 2010/048337 | 4/2010 |
| WO | 2010/115846 | 10/2010 |
| WO | 2010/115847 | 10/2010 |
| WO | 2011/056185 | 5/2011 |
| WO | WO 2011056185 A2 * | 5/2011 ......... C12N 15/1075 |
| WO | 2011/106460 | 9/2011 |

OTHER PUBLICATIONS

Search Report, UK Intellectual Property Office, Application. No. GB1119903.1, Mar. 15, 2012.
D Gorin et al., "Reactivity-dependent PCR: direct, solution-phase in vitro selection for bond formation", Journal of the American Chemical Society, vol. 131, No. 26, Jul. 2009, pp. 9189-9191.
SV Doronin et al., "Photoaffinity labeling of DNA polymerase alpha DNA primase complex based on the catalytic competence of a dNTP reactive analog", FEBS Letters, vol. 313, No. 1, 1992, pp. 31-33.
Search Report issued by the UK Patents Directorate regarding App. No. GB1119903.1, dated Mar. 15, 2012.
Goll & Bestor, Eukaryotic Cytosine Methyltransferases. *Annu. Rev. Biochem.* 2005, 74, 481-514.
Ito et. al. Role of Tet proteins in 5mC to 5hmC conversion, ES-cell self-renewal and inner cell mass specification. *Nature* 2010, 466: 1129-1133 (Published online Jul. 18, 2010).
Meissner et al. Epigenetic modifications in pluripotent and differentiated cells. *Nat. Biotech.* 2010, 28: 1079-1088.
Gommers-Ampt and Borst. Hypermodified bases in DNA. *FASEB J* 1995, 9, 1034-1042.
Schumacher et al. Microarray-based DNA methylation profiling: technology and applications. *Nucleic Acids Res* 2006, 34: 528-542.
Frommer et al., A genomic sequencing protocol that yields a positive display of 5-methylcytosine residues in individual DNA strands. *Proc Natl Acad Sci USA* 1992, 89: 1827-1831.
Huang et al. The Behaviour of 5-Hydroxymethylcytosine in Bisulfite Sequencing. *PLoS One* 2010, 5: e8888.
Weber et al. Chromosome-wide and promoter-specific analyses identify sites of differential DNS methylation in normal and transformed human cells. *Nat Genet* vol. 37, No. 8 (2005) pp. 853-862.
Rauch & Pfeifer. methylated-CpG Methylated-CpG island recovery assay: a new technique for the rapid detection of islands in cancer. *Lab. Invest.* 2005, 85: 1172-1180.
Liutkeviciute et al. Methyltransferase-Directed Derivatization of 5-Hydroxymethylcytosine in DNA. *Angew. Chem. Int. Ed.* 2011, 50, 2090-2093.
Liutkeviciute et al. Cytosine-5-methyltransferases add aldehydes to DNA. Nat. Chem. Biol. vol. 29, No. 5 (2009), pp. 400-402.

(Continued)

*Primary Examiner* — Aaron A Priest
(74) *Attorney, Agent, or Firm* — Cermak Nakajima & McGowan LLP; Shelly Guest Cermak

(57) ABSTRACT

A method for producing a nucleic acid molecule from a template nucleic acid sequence and a linking unit attached to a primer, which method comprises a step of contacting the template nucleic acid sequence with a nucleic acid polymerase under conditions which allow the nucleic acid polymerase to produce the nucleic acid molecule from the primer based on the template nucleic acid sequence, wherein the linking unit is attached to a target site in the template nucleic acid sequence with a covalent linkage.

36 Claims, 13 Drawing Sheets

(56) References Cited

OTHER PUBLICATIONS

Song et al. Selective chemical labeling reveals the genome-wide distribution of 5-hydroxymethylcytosine. Nat. Biotechnol. vol. 29, No. 1, Published online Dec. 12, 2010, pp. 68-72.
Pastor et al. Genome-wide mapping of 5-hydroxymethylcytosine in embryonic stem cells. Nature 2011, 473, 394-397 (published online May 8, 2011).
Morera et al. T4 Phage β-Glucosyltransferase: Substrate Binding and Proposed Catalytic Mechanism. J. Mol. Biol. 1999, 292, 717-730.
Larivière and Moréra. A Base-flipping Mechanism for the T4 Phage β-Glucosyltransferase and Identification of a Transition-state Analog, J. Mol. Biol. vol. 324 (2002), pp. 483-490.
Larivière et al. Structural Evidence of a Passive Base-flipping Mechanism for AGT, an Unusual GT-B Glycosyltransferase, J. Mol. Biol., vol. 352 (2005), pp. 139-150.
Kubo, et al. A Novel, Sensitive, and Specific Assay for Abasic Sites, the Most Commonly Produced DNA Lesion. Biochemistry, 1992, 31, 3703-3708.
Harris et al. Single-Molecule DNA Sequencing of a Viral Genome. Science, vol. 320 (2008), pp. 106-109. Supporting online materials: 26 pages.
Eid et al. Real-time DNA Sequencing from Single Polymerase Molecules. Science, 2009, 323:133-138.
International Search Report, Written Opinion PCT/EP2012/072934, dated Jan. 23, 2013 (13 pages).
Bowers et al. Virtual terminator nucleotides for next-generation DNA sequencing. Nat Methods, vol. 6, No. 8 (2009), pp. 593-595.
Djuric et al. Levels of 5-Hydroxymethyl-2'- Deoxyuridine in DNA from Blood as a Marker of Breast Cancer. Cancer, vol. 77, No. 4 (1996), pp. 691-696.
Gerasimaite et al. A directed evolution design of a GCG-specific DNA hemimethylase. Nucleic Acids Res., vol. 37, No. 21 (2009), pp. 7332-7341.
Hayatsu and Shiragami. Reaction of Bisulfite with the 5-Hydroxymethyl Group in Pyrimidines and in Phage DNAs. Biochemistry, vol. 18, No. 4 (1979), pp. 632-637.
Hermanson. Nucleic Acid and Oligonucleotide Modification and Conjugation. Bioconjugate Techniques, Academic Press, 1996, chapter 17, pp. 639-671.
Kriaucionis and Heintz. The Nuclear DNA Base 5-Hydroxymethylcytosine Is Present in Purkinje Neurons and the Brain. Sciencexpress, published online Apr. 16, 2009 (2 pages).
Lilley. Probes of DNA Structure. Methods Enzymol., vol. 212 (1992), pp. 133-139.
Lukinavicius et al. Targeted Labeling of DNA by Methyltransferase-Directed Transfer of Activated Groups (mTAG) J. Am. Chem. Soc. , vol. 129 (2007), pp. 2758-2759.
Neely et al. DNA fluorocode: A single molecule, optical map of DNA with nanometre resolution, Chem. Sci. vol. 1, No. 4 (2010), pp. 453-460, Supplementary Material.
Nielsen. Chemical and Photochemical Probing of DNA Complexes J. Mol. Recognition, vol. 3, No. 1 (1990), pp. 1-25.
Rokita. Chemical Reagents for Investigating the Major Groove of DNA Current. Protocols in Nucleic Acid Chemistry (2001): 6.6.1-6.6.16 (16 pages).
Rottach et al., DNA Methylation-Mediated Epigenetic Control. J. Cell. Biochem. vol. 108 (2009), pp. 43-51.
Sommer et al. Bacteriophage T4 α-glucosyltransferase: a novel interaction with gp45 and aspects of the catalytic mechanism Biochem. Biophys. Res. Commun., vol. 323 (2004), pp. 809-815.
Tahiliani et al. Conversion of 5-Methylcytosine to 5-Hydroxymethylcytosine in Mammalian DNA by MLL Partner TET1. Sciencexpress 324, published online Apr. 16, 2009 (pp. 930-935).
Surzycki (DNA Sequencing, in Human Molecular Biology Laboratory, Blackwell, 2003).
Prosecution of U.S. Appl. No. 2012/0094280 A1, published Apr. 19, 2012, U.S. Appl. No. 13/262,340 with Actions, Amendments, and References.
Restriction, U.S. Appl. No. 13/262,340 dated May 24, 2013, 6 pages.
Amendment Responsive to Office Action, U.S. Appl. No. 13/262,340 filed Apr. 14, 2014.
Prosecution of U.S. Appl. No. 2012/0088238 A1, published Apr. 12, 2012, U.S. Appl. No. 13/262,738 with Actions, Amendments, and References.
Restriction, U.S. Appl. No. 13/262,738 dated Jun. 20, 2013, 5 pages.
Amendment Responsive to Office Action, Office Action, U.S. Appl. No. 13/262,738 filed Mar. 21, 2014.
International Search Report and Written Opinion, PCT/EP2010/054436 dated Jul. 26, 2010, 10 pages.
International Preliminary Report on Patentability PCT/EP2010/054436 dated Oct. 4, 2011, 7 pages.
Cheng. Structure and Function of DNA Methyltransferases, Annual Review of Biophysics and Biomolecular Structure 24 (1995) 293-318.
Alegria. Hydroxymethylation of Pyrimidine Mononucleotides with Formaldehyde, Biochimica et Biophysica Acta 149 (1967) 317-324.
Flaks, et al. Virus-induced Acquisition of Metabolic Function. I. Enzymatic Formation of 5-Hydroxymethyldeoxycytidylate, Journal Biological Chemistry 234 (1959) 1501-1506.
Grafstrom et al. Pathobiological effects of acetaldehyde in cultured human epithelial cells and fibroblasts, Carcinogenesis 15 (1994) 985-990.
Bird, (2002), "DNA Methylation Patterns and Epigenetic Memory," Genes Dev. 16, 6-21.
Bong and Ghaderi, (2001), "Chemoselective Pd(0)-Catalyzed Peptide Coupling in Water," Org. Lett. 3, 2509-2511.
Cannon et al., (1988), "5-Hydroxymethylcytosine DNA Glycosylase Activity in Mammilian Tissue," Biochem. Biophys. Res. Commun. 151, 1173-1179.
Casalnuovo and Calabrese, (1990), Palladium-Catalyzed Alkylations in Aqueous Media, J. Am. Chem. Soc. 112, 4324-4330.
Dalhoff et al., (2006), "Direct Transfer of Extended Groups from Synthetic Cofactors by DNA Methyltransferase," Nat. Chem. Biol. 2, 31-32.
Dawson et al., (1994), "Synthesis of Proteins by Native Chemical Ligation," N-terminal cysteine residues of polypeptides, native chemical peptide ligation. Science 266, 776-779.
DeVasher et al., (2004), "Aqueous-Phase, Palladium-Catalyzed Cross-Coupling of Aryl Bromides under Mild Conditions, Using Water-Soluble, Sterically Demanding Alkylphosphines," J. Org. Chem. 69, 7919-7927.
Dibowski and Schmidtchen, (1998), "Bioconjugation of Peptides by Palladium-Catalyzed C-C Cross-Coupling in Water," Angew. Chem. Int. Ed. 37, 476-478.
Goll, "Eurkaryotic Cystosine Methyltransferases," M.G. & Bestor, T.H. Annu. Rev. Biochem. 74, 481-514 (2005).
Graham et al., (2002), "Internal Labeling of Oligonucleotide Probes by Diels-Alder Cycloaddition," Tet. Lett 43, 4785-4788.
Klimasauskas and Lukinavicius (2008), AdoMet-Dependent Methyltransferases, Chemistry of, Wiley Encyclopedia of Chemical Biology. DOI: 10.1002/9780470048672.wecb335, 1-10.
Klimasauskas and Weinhold, (2007), "A New Tool for Biotechnology: AdoMet-dependent methyltransferases," Trends Biotechnol. 25, 99-104.
Kutter and Wiberg, "Biological Effects of Substituting Cytosine for 5-Hydroxymethylcytosine in Deoxyribonucleic Acid of Bacteriophage T4," (1969) J. Virol. 4, 439-453.
LaFrancois et al. (1998), "Synthesis and Characterization of Isotopically Enriched Pyrimidine Deoxynucleoside Oxidation Damage Products," Chem. Res. Toxicol., 11, 75-83.
Lewis et al. (2002), "Click Chemistry In Situ: Acetylcholinesterase as a Reaction Vessel for the Selective Assembly of a Femtomolar Inhibitor from an Array of Building Blocks," Angew. Chem. Int. Ed. 41, 1053-1057.
Liu and Tam, (1994) "Peptide segment ligation strategy without use of protecting groups," Proc. Natl. Acad. Sci. USA 91, 6584-6588.

(56) References Cited

OTHER PUBLICATIONS

Merkiene and Klimasauskas, "Probing a rate-limiting step by mutational perturbation of AdoMet binding in the HhaI methyltransferase," (2005) Nucleic Acids Res. 33, 307-315.
Pignot et al., (2000), "Efficient Synthesis of S-Adenosyl-L-Homocysteine Natural Product Analogues and Their Use to Elucidate the Structural Determinant for Cofactor Binding of the DNA Methyltransferase M-HhaI," Eur. J. Org. Chem. 549-555.
Pljevaljcic et al., (2004), "Sequence-Specific Methyltransferase-Induced Labeling of DNA (SMILing DNA)," ChemBioChem 5, 265-269.
Pljevaljcic et al., (2003), "Design of a New Fluorescent Cofactor for DNA Methyltransferases and Sequence-Specific Labeling of DNA," J. Am. Chem. Soc. 125, 3486-3492.
Pljevaljcic et al., (2004), "Sequence-Specific DNA Labeling Using Methyltransferases," Methods Mol. Biol. 283, 145-161.
Poletayev et al., (1976) Mol. Biol. (Mosk),10, 682-685 (English Abstract).
Rusmintratip and Sowers (2000), An unexpectedly high excision capacity for mispaired 5-hydroxymethylated in human cell extracts, PNAS 97, 14183-14187.
Saxon and Bertozzi, (2000), "Cell Surface Engineering by a Modified Staudinger Reaction," Science 287, 2007-2010.
Tardy-Planechaud et al., (1997), "Solid phase synthesis and restriction endonuclease cleavage of oligodeoxynucleotides containing 5-(hydroxymethylated)-cytosine," Nucleic Acids Res. 25, 553-558.
Zhang et al.: (2006), "Natural Product Diversification using a Non-natural Cofactor Analogue of S-Adenoysl-L-methionine," J. Am. Chem. Soc. vol. 128, pp. 2760-2761.
Dalhoff, C. Novel S-adenosyl-L-methionine analogs with modifications in the methionine part for transalkylations with DNA-methyltransferases. Dissertation, RWTH Aachen University (2005), 14 pages (title and presentation pages (2 pages), Contents (7 pages), E2. Modifications to the activated side chain of AdoMet (5 pages noted as pp. 117-121)) (2005).
Garman A., Non-Radioactive Labeling: A Practical Introduction, Biological Techniques Series, Academic Press (1997), pp. 1-132.
Ignashov VG., Influence of Antibodies Against DNA on the Renaturation of DNA., Mol Biol (Mosk). Jul.-Aug. 1976;10(4): 682-685. (Abstract only).
House H.O. Modern synthetic reactions, 2nd ed., W.A. Benjamin, NY, 1972 pp. 353-363.
International Search Report and Written Opinion, PCT/EP2010/054437 dated Jul. 19, 2010, 11 pages.
International Preliminary Report on Patentability PCT/EP2010/054437 dated Oct. 4, 2011, 7 pages.
User Guide entitled "EpiQuikTM DNA Methyltransferase Activity/Inhibition Assay Kit," Catalog No. P-3001, Version 3.1006, http://www.epigentek.com/docs/P-3001.pdf (Jan. 25, 2008).
Roll et al., DNMT3b overexpression contributes to a hypermethylator phenotype in human breast cancer cell lines, Molecular Cancer, Biomed Central 7 (2008), 14 pages.
Hayatsu et al. Reaction of Bisulfite with the 5-Hydroxymethyl Group in Pyrimidines and in Phage DNAs, Biochemistry 18 (1979) 632-637.
Cheng, (1995), "Structure and Function of DNA Methyltransferase," Annu. Rev. Biophys. Biomol. Struct. 24, 293-318.
Djuric, Z. et al. (1996), "Levels of 5-Hydroxymethyl-2'-Deoxyuridine in DNA from Blood as a Marker of Breast Cancer," Cancer 77, 691-696.
Gieselman et al. (2002), "Selenocysteine Derivatives for Chemoselective Ligations," ChemBioChem 3, 709-716.
Penn et al., (1972), "The Presence of 5-Hydroxymethylcytosine in Animal Deoxyribonucleic Acid," Biochem. J. 126, 781-790.
Schumacher et al., (2006), "Microarray-based DNA methylation profiling: technology and applications," Nucleic Acids Res. 34, 528-542.
Valinluck, V. et al., (2004), "Oxidative damage to methyl-CpG sequences inhibits the binding of the methyl-CpG binding domain (MBD) of methyl-CpG binding protein 2 (MeCP2)," Nucleic Acids Res. 32, 4100-4108.
Wong et al., (2005), "Phenotypic differences in genetically identical organisms: the epigenetic perspective," Hum Mol Genet 14, R11-R18.
Wirth, T. (2000), "Organoselenium Chemistry in Stereoselective Reactions," Angew. Chem. Int. Ed. 39, 3741-3749.
Zelakiewicz et al., "Observation of Selenium-77 Nuclear Magnetic Resonances in Octaneselenol-Protected Gold Nanoparticles," *J. Am. Chem. Soc.*, 2004, 126, 8112-8113.

\* cited by examiner

NUCLEIC ACID PRODUCTION AND SEQUENCE ANALYSIS

This application is a continuation of co-pending U.S. Ser. No. 13/679,538 filed Nov. 16, 2012, now U.S. Pat. No. 9,347,093 issued May 24, 2016; which claims priority to Great Britain Application Serial No. 1119903.1 filed Nov. 17, 2011; each of which is hereby expressly incorporated by reference herein in its entirety.

FIELD OF THE INVENTION

The present invention relates to methods of producing nucleic acid molecules with nucleic acid polymerases and to the use of the methods in sequence analysis at modification sites of nucleic acids.

BACKGROUND

Post-transcriptional covalent modifications of DNA are important epigenetic factors in mammalian development and disease (Goll & Bestor, *Annu. Rev. Biochem.* 2005, 74, 481-514). The best known DNA modification is methylation of cytosine residues at the C5 position (5 mC) which occurs predominantly in the context of CG dinucleotides in all vertebrates including humans (Rottach et al., *J. Cell. Biochem.* 2009, 108: 43-51). Recent studies of genomic DNA from the human brain, neurons and from mouse embryonic stem cells provided evidence that CG sequences also contain 5-hydroxymethylcytosine (hmC) (Tahiliani et al., 2009, *Science*, 324: 930-935; Kriaucionis & Heintz, 2009, *Science*, 324: 929-930). Increasing evidence (Ito et. al., *Nature* 2010, 466: 1129-1133) suggests that hmC may also play important epigenetic roles in embryonic development, brain function and cancer progression. In particular, elevated levels of 5-hydroxymethyluracil (hmU), a deaminated version of hmC in DNA, were reported to correlate with incidents of breast cancer (Djuric et al., *Cancer*, 1996, 77, 691-696). Glucosylated forms of 5-hydroxymethylated bases in certain bacteriophages and an African *trypanosome* serves to protect the invading genome against host defense systems (Gommers-Ampt and Borst, *FASEB J*, 1995, 9, 1034-1042). Bacterial and archaeal organisms contain genomic N6-methyladenine and N4-methylcytosine along with 5 mC. These methylated bases are also involved in species-specific control of genetic exchange as well as regulation of important genes related to pathogenicity.

Numerous techniques have been developed for the identification and localization of 5 mC in DNA (Schumacher et al., *Nucleic Acids Res*, 2006, 34: 528-542). Most of the analytical approaches of the latter group can be divided into two major types: bisulfite conversion-based techniques, and non-covalent affinity binding-based techniques (i.e. immunoprecipitation). The gold standard method to study the genomic localization of individual 5 mC residues is bisulfite sequencing and its numerous modifications. This method is based on bisulfite-mediated deamination of C to U; 5 mC and hmC residues are inert to this reaction, and therefore standard sequencing of bisulfite-converted DNA shows the modified residues in the C-track, whereas T and C residues appear in the T-track (Frommer et al., *Proc Natl Acad Sci USA*, 1992, 89: 1827-1831) (Hayatsu & Shiragami, *Biochemistry*, 1979, 18: 632-637; Huang et al., *PLoS One*, 2010, 5: e8888.). The method provides the highest mapping resolution (single nucleotide), but suffers from the following shortcomings:

1) conversion of the tetranucleotide sequences into trinucleotides DNA sequences often precludes unequivocal assignment of sequence reads to genomic loci; and 2) the procedure is tedious, labor-intensive and prone to experimental artefacts.

Among the affinity-based techniques, MeDIP and MethylCap are the most widely used. MeDIP uses an antibody that is specific for 5-methylcytosine to retrieve methylated fragments from sonicated genomic DNA (Weber et al., *Nat Genet,* 2005, 37: 853-862). MethylCap employs a methyl-binding domain protein to obtain methylated DNA fractions (Rauch & Pfeifer, *Lab. Invest.* 2005, 85: 1172-1180). Antibodies against hmC have been produced which non-covalently bind hmC-containing DNA fragments (Ito, S. et al., *Nature,* 2010, 466: 1129-1133; Meissner et al., *Nat. Biotech.* 2010, 28:1079-1088). All these techniques permit enrichment of modified cytosine-containing fragments from pools of genomic DNA fragments for further analysis using DNA sequencing or hybridization to DNA microarrays. A major limitation of these approaches is their low resolution which is defined by the minimal size of a DNA fragment that can be amplified using PCR (typically 200-500 base pairs).

Another group of methods to study DNA modification use covalent tagging of target sites. Genomic fragments containing unmodified methyltransferase sites can be selectively labelled and separated from modified fragments using mTAG (Lukinavicius et al. *J. Am. Chem. Soc.* 2007, 129, 2758-2759, EP1874790) or similar approaches (EP1102781, EP1756313, U.S. Pat. No. 7,465,544). Analysis of hmC residues can be similarly accomplished using methyltransferase-directed derivatization and labelling (WO2010115846; WO2010115847; Liutkeviciute et al., *Angew. Chem. Int. Ed.,* 2011, 50, 2090-2093) or using glucosyltransferases for transfer of derivatized sugars (Song et al., *Nat. Biotechnol.* 2010, 29, 68-72; Pastor et al., *Nature* 2011, 473, 394-397) followed by covalent labelling with reporters such as biotin. These techniques permit enrichment of labelled fragments from pools of genomic DNA fragments for further analysis using DNA sequencing or hybridization to DNA microarrays. As mentioned above, the resolution is again defined by the minimal size of a DNA fragment that can be amplified using PCR (typically 200-500 base pairs).

It is an aim of the present invention to solve one or more of the problems with the prior art described above and to provide further methods of sequence analysis at modification sites of nucleic acids.

SUMMARY OF THE INVENTION

In a first aspect the present invention provides a method for producing a nucleic acid molecule from a template nucleic acid sequence and a linking unit attached to a primer, which method comprises a step of contacting the template nucleic acid sequence with a nucleic acid polymerase under conditions which allow the nucleic acid polymerase to produce the nucleic acid molecule from the primer based on the template nucleic acid sequence, wherein the linking unit is attached to a target site in the template nucleic acid sequence with a covalent linkage.

The present inventors have surprisingly found that primers that are covalently tethered to a target site in a template nucleic acid sequence can prime a nucleic acid polymerase reaction at their 3' ends starting at or around the target site.

This surprising finding can be utilised to produce nucleic acid from a template nucleic acid molecule in the absence of a primer that recognises and binds to the template through non-covalent complementary base pairing alone. For example, the method of the present invention can be used where it is necessary to prime a nucleic acid polymerase reaction in the absence of sequence information that would allow the design of a complementary primer, or when the use of a long primer is not desirable.

Further, the method of the invention can most advantageously be used in the analysis of covalent modifications of nucleic acid sequence, and in particular DNA methylation. Accordingly, the present invention provides the use of the method of the first aspect of the invention to determine the presence or absence of a nucleotide modification in a nucleic acid molecule.

The method of the invention can also be suited to query whether/which target sites are available for covalent modification. Sites can be blocked by other bound molecules (not only covalent methylation), or some sites can be inaccessible due to internal interactions with other parts of the same molecules (ternary interactions). This information may be useful for determining functionally important interactions of nucleic acids molecules in vitro or in living cells ex vivo. Subsequent priming to produce nucleic acid molecules, and sequencing, will directly reveal all available sites (the kind of footprint methods that is coupled with sequencing) and by inference will point to all sites that are inaccessible.

In a preferred embodiment the present invention provides a method for determining the presence or availability of a target site comprising a nucleotide within a template nucleic acid sequence, which method comprises:

(a) contacting the template nucleic acid sequence with a compound comprising a first reactive group and an enzyme, wherein the enzyme is capable of transferring the first reactive group, or a part of the compound comprising the first reactive group, onto the nucleotide;

(b) contacting the nucleic acid sequence with a second reactive group attached to a linking unit, optionally wherein a primer is attached to the linking unit, under conditions that allow the first reactive group to react with the second reactive group to form a covalent linkage;

(c) optionally, where the primer is not attached to the linking unit in step (b), binding a primer to the linking unit;

(d) contacting the nucleic acid sequence and the primer with a nucleic acid polymerase under conditions which allow the nucleic acid polymerase to produce a nucleic acid molecule from the primer based on the template nucleic acid sequence;

(e) detecting the presence or absence of the produced nucleic acid molecule so as to determine the presence or availability of the target site.

Accordingly, the detection of the presence of a produced nucleic acid molecule indicates the presence and the availability of the target site, i.e. can directly serve as a primary locus-specific identifying signal. In contrast, the absence of the produced nucleic acid molecule indicates the absence and/or non-availability of the target site.

It is particularly preferred that the method of this embodiment further comprises a step of sequencing the produced nucleic acid molecule so as to provide site-specific information and determine the sequence context at the target site, i.e. the origin of the produced nucleic acid molecule, providing an additional layer of information.

In the prior art, primer specificity is obtained through complementary base pairing with a segment of the template nucleic acid sequence. Such binding is usually unable to distinguish modified and unmodified nucleic acid sequence, particularly in the case of DNA methylation and hydroxymethylation. In contrast, in a preferred embodiment of the present invention a primer can be attached to the template nucleic acid sequence based on the modification state of a nucleotide within the sequence. Accordingly, the production of nucleic acid molecule by a polymerase from the primer is indicative of the modification state of the nucleotide. The proximity effect of the primer covalently attached via the linking unit to the nucleotide permits a different mechanism of priming which does not require extensive base pairing of the primer with the template. If the sequence of the template nucleic acid sequence is known then single nucleotide resolution mapping of the modification site to the reference genome can be achieved. If the reference sequence is not known, sequence context of modification sites can be determined, which may be useful for determining the specificity (consensus sequence) of the modification enzyme. Thus the method of the invention provides a new and useful tool for high resolution mapping of modification states in nucleic acids, and in particular in genomic DNA.

In a further aspect the present invention provides a kit for use in producing a nucleic acid molecule comprising:

(a) an enzyme capable of covalent derivatization of a nucleotide in a nucleic acid sequence with a first reactive group;

(b) a compound comprising the first reactive group;

(c) a linking unit attached to a second reactive group; and (d) optionally a nucleic acid polymerase enzyme.

In a third aspect the present invention provides the use of a linking unit and a primer for priming a nucleic acid polymerase reaction, wherein the linking unit is attached to a target site in a nucleic acid sequence with a covalent linkage Still further, the present invention provides a template nucleic acid sequence attached to a linking unit and a primer, wherein the linking unit is attached to a target site in the template nucleic acid sequence with a covalent linkage.

BRIEF DESCRIPTION OF THE DRAWINGS

The invention will be described in more detail with reference to the Figures in which.

DETAILED DESCRIPTION

Figure 1:
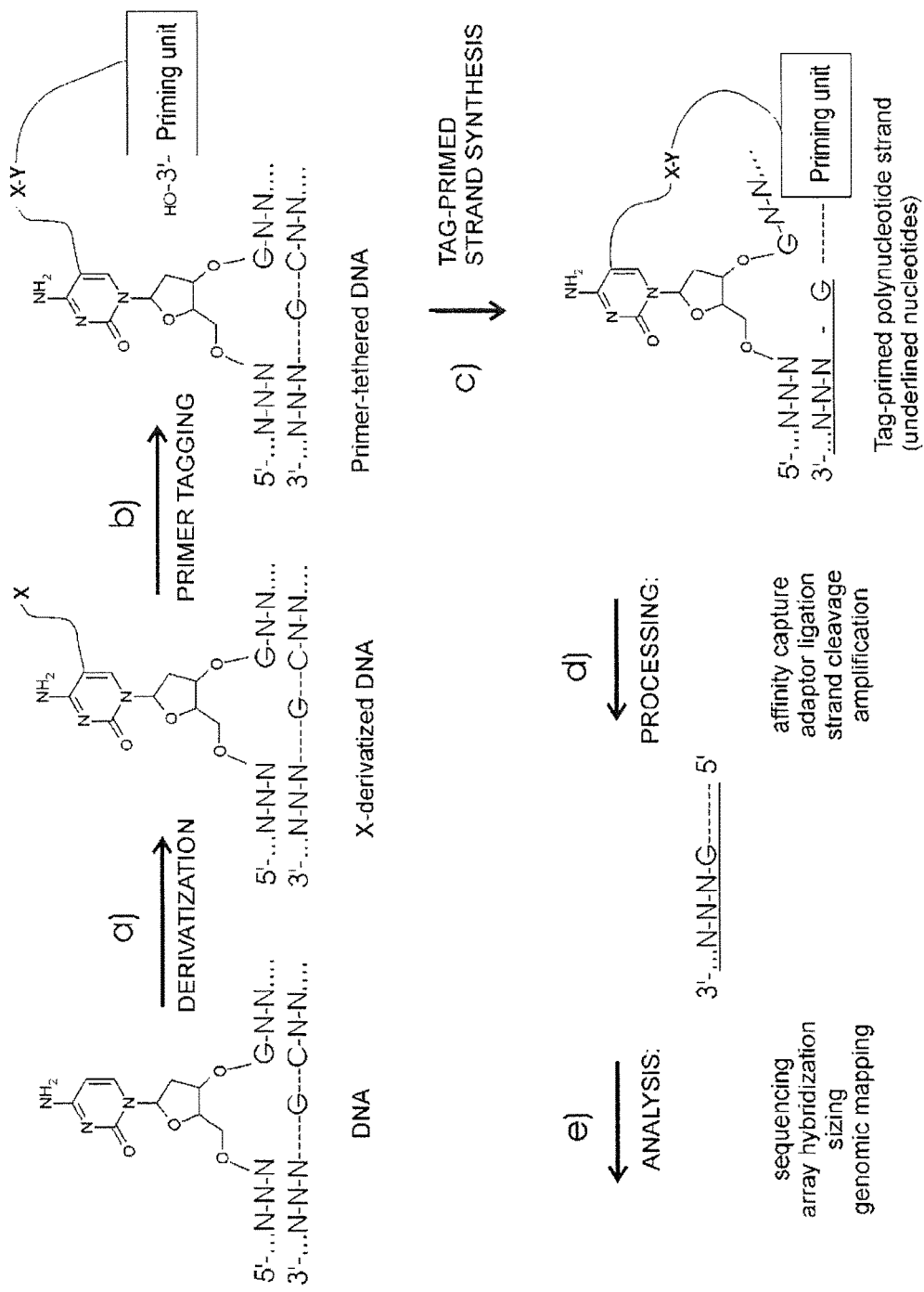
FIG. 1 shows a general scheme for mapping of covalently tagged target sites in DNA.

The present invention relates to a method for producing a nucleic acid molecule from a template nucleic acid sequence and a linking unit attached to a primer, which method comprises a step of contacting the template nucleic acid sequence with a nucleic acid polymerase under conditions which allow the nucleic acid polymerase to produce the nucleic acid molecule from the primer based on the template nucleic acid sequence, wherein the linking unit is attached to a target site in the template nucleic acid sequence with a covalent linkage.

Further, the present invention relates to a template nucleic acid sequence attached to a linking unit and a primer, wherein the linking unit is attached to a target site in the template nucleic acid sequence with a covalent linkage.

In the present invention a primer is attached to a linking unit that is itself attached via a covalent linkage to a target site in a template nucleic acid sequence, for priming a nucleic acid polymerase reaction. It is noted that the linking unit is a separate entity to the template nucleic acid sequence and the present invention is not related to prior art methods in which the 3' end of the template nucleic acid sequence self-primes by looping back and annealing to an internal sequence of the template (such as in headloop PCR), i.e. the method of the present invention does not involve hairpin priming. Such methods require extensive base-pairing between the primer and the template in order for polymerisation to be initiated. In other words, in the present invention the linking unit does not comprise nucleic acid sequence which is an extension of the template nucleic acid sequence.

Further, preferably the method of the present invention does not involve the linking unit being attached with the covalent linkage to a terminal nucleotide of the template nucleic acid sequence, such that priming of nucleic acid molecule production using a nucleic acid polymerase and the primer attached to the linking unit creates a hairpin structure, such as described in WO2011/056185 and Gorin et al., *J. Am. Chem. Soc.* 2009, 131, 9189-9191. In particular, in the method of the present invention the covalent linkage is formed based on the sequence or feature of the template nucleic acid sequence at the target site, which does not cause the cleavage of the template nucleic acid molecule to form a different shorter nucleic acid molecule with the linking unit attached at one end.

The primer in the present invention does not require extensive base pairing with the template nucleic acid in order to prime the polymerisation reaction, although it is preferred that the primer comprises at least one nucleotide, and more preferably at least two nucleotides at its 3' end which are capable of base pairing with nucleotides of the template nucleic acid sequence and preferably within or adjacent the target site. In particular in one embodiment of the invention the primer comprises four nucleotides or less complementary to the template nucleic acid at the start point of production of the nucleic acid molecule by the nucleic acid polymerase (e.g. adjacent to the 5' end of the produced nucleic acid molecule, or at the target site or adjacent thereto). Preferably in this embodiment the primer comprises two nucleotides or less complementary to the template nucleic acid at the start point of production of the nucleic acid molecule by the nucleic acid polymerase. It is preferred that the polymerised strand starts at the target site, or within less than 5 bases of the target site.

The primer (also referred to herein as the "tag-primer" or "tethered primer" when attached via the linking unit to the template nucleic acid sequence) comprises a length of nucleotide sequence. This may contain natural or chemically modified DNA, RNA nucleotides (such as LNA for example) and strands comprising such nucleotides in various combinations. The primer may also comprise PNA (peptide nucleic acid) and include any nucleic acid strands that permit priming of template-dependent strand synthesis by DNA or RNA polymerases.

Figure 2:
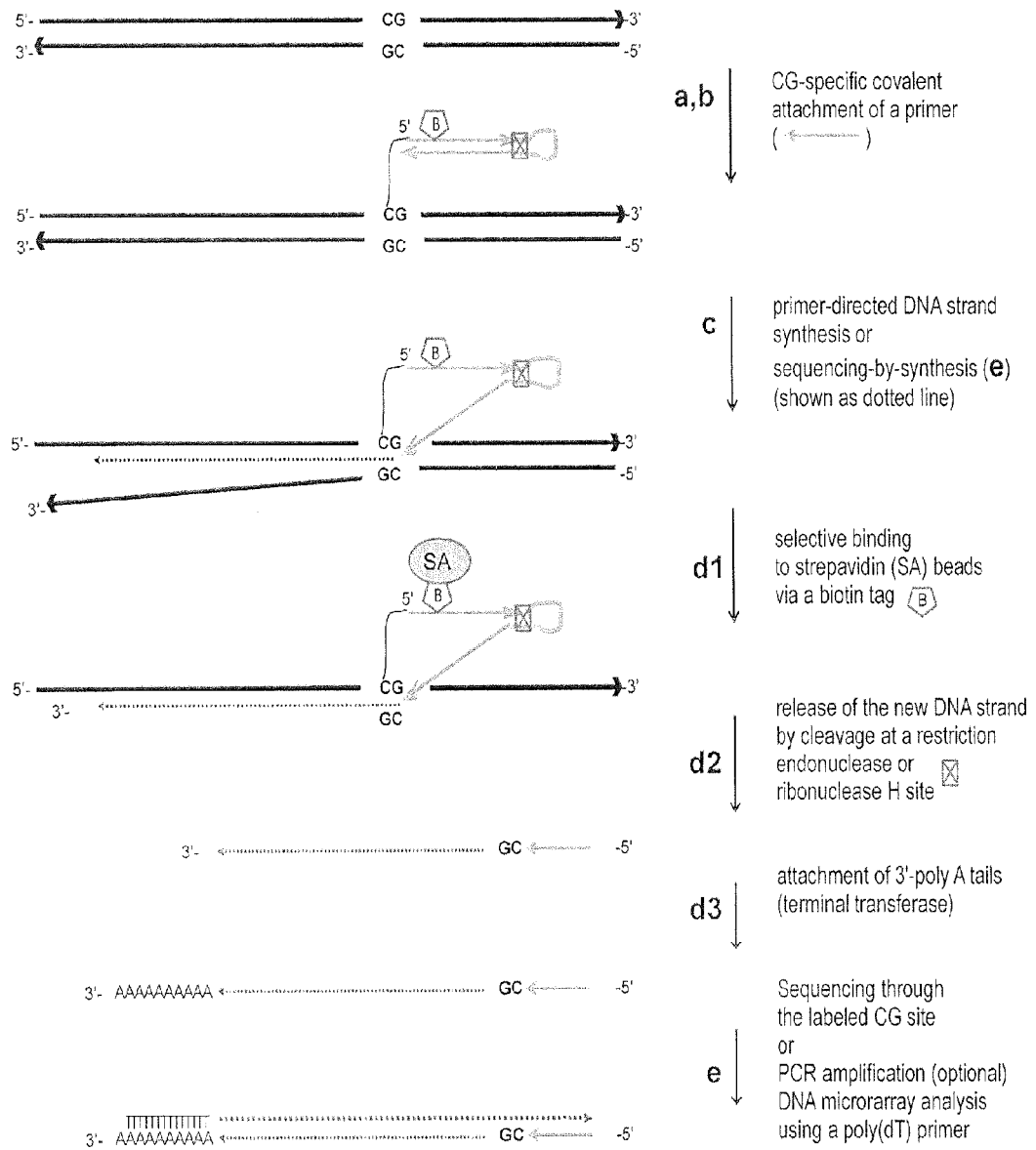
FIG. 2 shows a scheme for whole genome mapping of modifiable CG target sites (3' polyA tail (SEQ ID NO: 18) and polyd(T) primer (SEQ ID NO: 19)).
Figure 3:
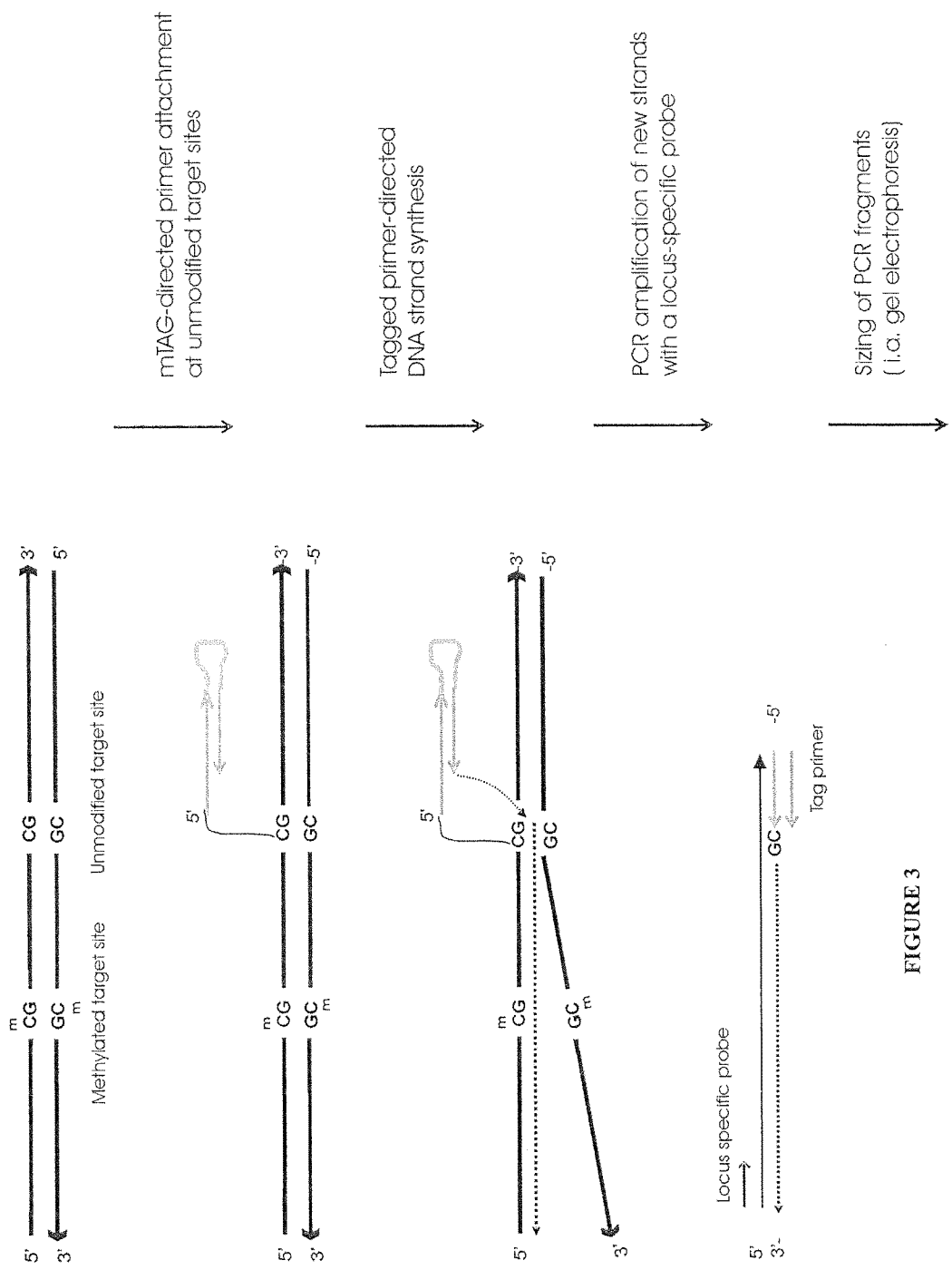
FIG. 3 shows a scheme for locus-specific mapping of unmodified target sites in DNA by sizing PCR products.

Correct positioning of the primer adjacent to the template nucleic acid sequence at the position where it is desired for polymerisation to begin, can be achieved by adjusting the size of the linking unit or by adjusting the size of the primer. Accordingly, the primer can be as short as one, two or three nucleotides in length or can be as large as 100 nucleotides. However, preferably the primer is between 10 to 20 nucleotides in length. This enables amplification of the extended strand using a matching external primer as shown in FIGS. 2 and 3. The at least one, preferably at least two, nucleotides at the 3' end of the primer can be chosen based on the identity of the nucleotide(s) at the target site to which the primer is to be attached. For example, if the target side includes a nucleotide which is part of a CpG site, the a G and/or C residue may be included in the 3' end of the primer.

The primer may preferably contain homonucleotide sequences (like a stretch of A nucleotides) at or near its 3'-terminus. Homopolymeric structures are known to readily form slipped hybridization products (duplexes) which may permit the 3'-terminal nucleotide to assume a favourable position for the priming of template dependent strand synthesis by DNA polymerase.

Figure 4:
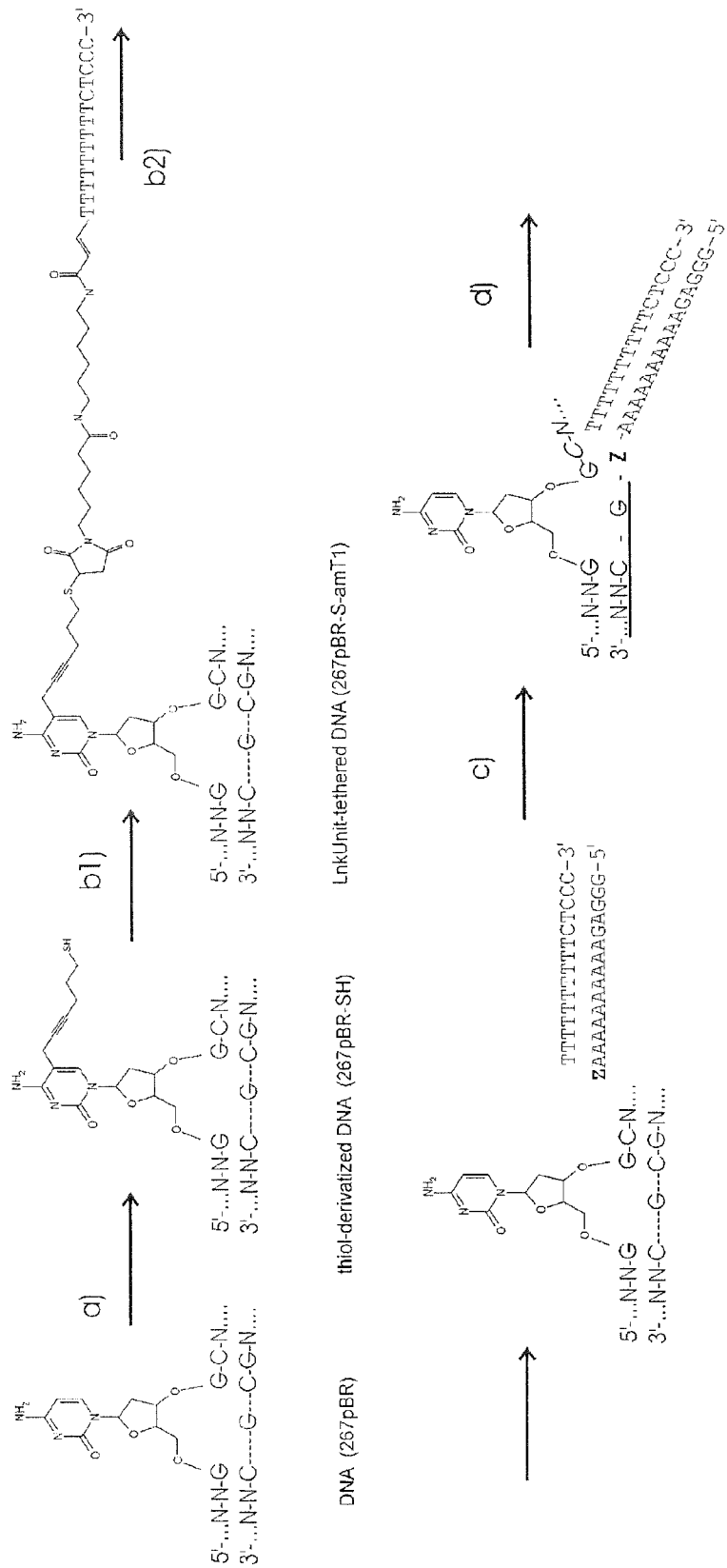
FIG. 4 shows a strategy for sequence mapping of covalently tagged GCGC sites in a DNA fragment (LnkUnit-tethered DNA (SEQ ID NO:20).

The primer is attached at its 5' end or 5' portion to a linking unit. The purpose of the linking unit is to join the primer to the target site, and can be used to achieve the correct positioning of the primer relative to the desired start point of polymerisation. The overall length may also vary but optimally should permit sufficient physical interaction of the 3-end of the primer with the target site. It may vary in chemical nature (linear, branched, or containing cyclic moieties). The linking unit generally comprises an organic molecule and can be a short polymer. An example of a suitable linking unit is shown in FIG. 4. Specifically, the linking unit can be a hydrocarbon chain optionally containing one or more heteroatoms (e.g. S or N) or aromatic or alicyclic rings. The chain length between the nucleotide (or abasic nucleotide) of the template nucleic acid sequence, to which the linking unit is attached at one end, and the nucleotide sequence of the primer or nucleotide sequence of the linking unit to which the primer is attached, may be from 5 to 40, preferably from 10 to 35 and most preferably from 20 to 30 atoms in length. These atoms may be substituted or unsubstituted, or attached to side chains, provided the length of these side chains does not interfere with the interaction of the primer with the template nucleic acid sequence.

The primer (also referred to herein as "priming unit") can be covalently or non-covalently attached to the linking unit. Where the attachment is non-covalent the linking unit may comprise a nucleic acid strand (oligonucleotide), and the methods of the invention described herein may require an additional step of binding the primer to the linking unit. Non-covalent bonding preferably involves base pairing interactions between the oligonucleotide of the linking unit and the externally added primer. Such inter strand interactions may be due Watson-Crick base pairing, or due to other types of pairing interactions such as those found in aptamers and large RNA. In these embodiments the primer should be at least 10 nucleotides, and preferably at least 15 nucleotides in length in order to allow for a section of the primer to be involved in base pairing with the linking unit.

In this embodiment, the primer and the linking unit may preferably form a molecular structure that resembles a double helix found in DNA or RNA duplexes, which may favourably interact with a DNA polymerase and thus facilitate the initiation of template-dependent strand synthesis at the 3'-end of the primer.

Other non-covalent linkages between the primer and the linking unit may be used to tether the primer. For example, non-covalent interactions may be utilised such as biotin-avidin binding, and antigen-antibody binding.

Suitable conditions for the additional step of binding the primer to the linking unit in the methods of the present invention are known in the art.

Where the primer is covalently attached to the linking unit, that may be via any stable covalent linkage connecting to a nucleobase or the phosphodiester-sugar backbone (preferably at its 5'-end) of the primer. If the linking unit comprises an oligonucleotide, the oligonucleotide and the primer may comprise a continuous oligonucleotide strand. The unified oligonucleotide strand may contain deoxyribonucleotide units, ribonucleotide units, modified ribonucleotide units (e.g. LNA, etc).

In a preferred embodiment the linking unit or the primer referred to herein further comprises an affinity binding group which permits separation of the linking unit and/or primer and/or whatever they are bound to. In a preferred embodiment the affinity group allows a complex comprising the template nucleic acid sequence, the linking unit, the primer and the newly produced nucleic acid molecule to be separated from the rest of the nucleic acid material such as non-template strands and unmodified fragments. Suitable affinity tags are known in the art. Examples are tags based on streptavidin, biotin, and peptide tags which bind to antibodies.

Where an affinity tag is used the methods of the present invention can include an additional step of separating produced nucleic acid sequence comprising the affinity tag. In particular, after the complex of the produced nucleic acid sequence and the primer, linking unit and template nucleic acid sequence is bound to, for example, the streptavidin beads, via the affinity tag, the newly synthesized strands can be selectively released by detaching it from the rest of the complex. This can be done, for example, by cleavage with a restriction endonuclease or a nickase at a built-in target site (see FIG. 2), or by cleavage with ribonuclease (or cleavage alkali cleavage) at a ribonucleoside residue in the oligonucleotide part of the linking unit, or by using any other method such as chemical cleavage of a chemical bond under mild conditions, or photo-induced cleavage.

The nature of the template nucleic acid sequence is not particularly limited. The template nucleic acid sequence can be DNA or RNA. Typically the template nucleic acid sequence is from double-stranded DNA, and can be genomic DNA. As described herein, a preferred embodiment of the present invention relates to the study of DNA modifications, particularly in genomic DNA. Alternatively the template nucleic acid sequence may be single-stranded DNA. Preferably the template nucleic acid sequence is less than 500 bp but more than 20 bp in length, more preferably in the range of 50 to 200 bp.

In a preferred embodiment the template nucleic acid sequence comprises oligonucleotide segments. The oligonucleotide segments are not especially limited and are simply sub-sequences or sections of a larger nucleic acid molecule. The segments may be formed by mechanical methods or by enzymatic or chemical digestion of nucleic acid. The segments are preferably formed by DNA shearing. The oligonucleotide segments are usually double stranded. Typically, the segments formed have random ends (a mixture of 3'- and 5'-extensions and blunt-ends). Such segments can be blunt-ended using a DNA polymerase that possesses both the 5'-overhang fill-in and of 3'-overhangs removal activities, e.g. T4 DNA polymerase).

An adaptor nucleic acid sequence may be added to either the 5' or 3' ends or both ends of each segment, wherein each adaptor sequence is capable of hybridizing with a primer for a polymerase chain reaction. Typically, the segments formed have blunt ends, and an adaptor nucleic acid sequence is ligated to each of the 5' and 3' blunt ends. Alternatively, the segments have sticky ends, and the adaptor nucleic acid sequence is ligated to the sticky ends. The skilled person will be well aware of suitable methods for ligating adaptor sequences to nucleic acid segments. Suitable ligation enzymes include but are not limited to EC 6.5.1.1 class enzymes originating from bacteriophage (T4), bacterial and mammalian (ligases I to IV) sources.

Alternatively, segments can be extended by adding multiple nucleotides (homopolymeric sequences such as poly dT) at their 3'-ends using terminal deoxynucleotidyl transferases; primers comprising complementary homooligonucleotide ((dA)n) sequences are then used during PCR amplification or for direct sequencing in sequencing devices such as HellScope™ Single Molecule Sequencer (Helicos BioSciences Corporation) (Harris et al. *Science,* 2008, 320, 106-109; Bowers et al. *Nat Methods,* 2009, 6, 593-595).

The linking unit is attached with a covalent linkage to the template nucleic acid sequence at a target site in the sequence. Accordingly, the methods of the invention described herein can comprise a step of forming this covalent linkage.

In a preferred aspect of the invention, as indicated above, the step of forming the covalent linkage does not involve a step of cleaving the template nucleic acid sequence, but the covalent linkage is formed based on the sequence or feature of the template nucleic acid sequence at the target site. Further the covalent linkage is specifically formed at the target site without the need for complementary binding between the template nucleic acid sequence and the primer. As such, the step of forming the covalent linkage can occur prior to the step of contacting the primer with the template nucleic acid molecule. In other words, the covalent linkage is formed in the absence of annealing of the primer to the template nucleic acid sequence.

As explained in more detail below, the step of forming the covalent linkage may be performed using a transferase enzyme, and in particular, using a transferase enzyme to transfer a reactive group onto the template nucleic acid sequence at the target site.

In particular, the covalent linkage can be formed in one step or in two steps, (for example steps (a) and (b) as shown in FIGS. 1 and 4).

Where a two-step procedure is used the method of the present invention may utilise as the starting material a template nucleic acid sequence in which a target site has already been derivatized with a first reactive group. Accordingly, the method comprises a step of forming the covalent linkage by contacting the target site, derivatized with a first reactive group, with a second reactive group attached to the linking unit under conditions that allow the first reactive group to react with the second reactive group to form the covalent linkage. Alternatively, the method of the present invention may utilise as the starting material a template nucleic acid sequence and begin with a step of derivatizing the target site in the template nucleic acid sequence with a first reactive group.

The first step of derivatization can be done using an enzymatic or a chemical reaction, and involves derivatization of a nucleotide or an abasic nucleotide within the target site.

Methods for the first step of covalent derivatization of the starting template nucleic acid sequence are known in the art. Derivatization can be carried out in vitro (on isolated nucleic acids) or ex vivo, in living cells, cell extracts etc., and can be done using an enzymatic or a chemical reaction to derivatize a nucleotide or an abasic nucleotide within the target site. In particular, enzymes can be used to transfer modification/derivatisation groups onto a nucleotide within the target sequence, preferably based on a target site/sequence within the template nucleic acid sequence.

Preferably the derivatization step comprises contacting the template nucleic acid sequence with a compound and an enzyme, wherein the compound comprises the first reactive group, and wherein the enzyme is capable of transferring the first reactive group or a part of the compound comprising the first reactive group onto a nucleotide in the target site.

The enzyme may comprise a methyltransferase or a glucosyltransferase. Preferably the enzyme is a DNA methyltransferase and is used when the template nucleic acid sequence is DNA. Suitable DNA methyltransferases can be C-5 methyltransferases or the amino methyltransferases N4 cytosine methyltransferase or N6 adenine methyltransferase.

The C-5 DNA methyltransferase enzymes can be generally chosen from M.HhaI, M.HpaII, M.GCG, M.SssI, and M2.Eco31I, or modified variants of these enzymes, such as HhaI DNA methyltransferase variant Q82A/Y254S/N304A, that are adapted to work with synthetic cofactors. M.GCG (or M.HhaI dL2-14) is a derivative of M.HhaI with engineered sequence specificity to recognize GCG target sites (Gerasimaite et al., 2009, *Nucleic Acids Res.* 37, 7332-7341).

The amino methyltransferases can be the adenine-N6 specific DNA methyltransferases M.TaqI (TCGA), M.RsrI (GAATTC), or M.BseCI (ATCGAT)— or the cytosine-N4 specific methyltransferases M.BcnIB (CCSGG), M2.BfiI (ACTGGG). Based on structural modelling a mutant of M.TaqI has been produced (V21G in motif IV) which also shows a higher alkylation efficiency than the WT enzyme (EP1874790). M.TaqI has proven to be efficient with different factor analogs.

Preferably, in the methods described herein, the DNA methyltransferase enzyme is M.SssI, M.MpeORF4940P (CG), M.HhaI (GCGC), M.HpaII (CCGG), M.HsaDnmt1, M.HsaDnmt3A, M.HsaDnmt3B, M.MmuDnmt1, M.MmuDnmt3A, M.MmuDnmt3B (CG), M.HaeIII (GGCC), M.CviJI (RGCB), M2.Eco31I. (GGTCTC), M.EcoRII, M.EcoDcm, M.MvaI, M.BstNI (CCWGG), M.TaqI (TCGA), M.BseCI (ATCGAT), M.Ecodam, T4Dam (GATC), M.RsrI, or M.EcoRI (GAATTC). Further details of these, and other methylatransferase enzymes, can be found in the online REBASE database.

Where a methyltransferase is utilized, a cofactor based on S-Adenosyl-L-methionine (SAM or AdoMet) can be used as the compound comprising the first reactive group. Suitable SAM analogues are known in the art and in particular, are described in WO2006/108678, Lukinavicius et al. *J. Am. Chem. Soc.* 2007, 129, 2758-2759, and in Neely et al., (Chem. Sci., 2010, 1, 453-460). In particular, the prior art describes:

1. Covalent derivatization of unmodified cytosine or adenine residues (such as CG, GCGC, TCGA,—although the specificities can be broader since 2-8 nucleotide sequences are recognized by DNA methyltransferases, listed in REBASE) in genomes using methyltransferase-directed transfer of activated groups (mTAG) containing a reactive group (Lukinavicius et al. *J. Am. Chem. Soc.* 2007, 129, 2758-2759, EP1874790) or using similar approaches (EP1102781, U.S. Pat. No. 7,465,544); and 2. Covalent derivatization of 5-hydroxymethyl cytosine (hmC) residues at target sites (CG, GCGC etc) using methyltransferase-directed derivatization with a reactive group (WO2010115846; WO2010115847; Liutkeviciute et al., *Angew. Chem. Int Ed.*, 2011, 50, 2090-2093).

Where a glucosyltransferase is used, typically the enzyme is alpha glucosyltransferase or beta glucosyltransferase (AGT or BGT glucosyltransferase). These enzymes have been found in T-even bacteriophages whereby hmC residues are converted to Glc-hmC residues in DNA (Gommers-Ampt & Borst, *FASEB J.* 9, 1034-1042 (1995); Morera et al. (1999) *J. Mol. Biol.* 292, 717-730; Lariviere, L. & Morera, S. (2002). *J. Mol. Biol.* 324, 483-490.; Sommer et al. (2004) *Biochem. Biophys. Res. Commun.* 323, 809-815; Lariviere et al., *J. Mol. Biol.* (2005) 352, 139-150). When these enzymes react with hydroxymethylcytosine in the presence of a compound comprising a glucosyl group, α-glucosyl-hydroxymethyl cytosine or β-glucosyl-hydroxymethyl cytosine are formed respectively.

Covalent derivatization of 5-hydroxymethylcytosine residues using glucosyltransferase-directed transfer of modified glucose moieties containing a reactive group such as described in Song et al., *Nat. Biotechnol.* 2010, 29, 68-72 (using the groups azide and alkyne) or in Pastor et al., *Nature* 2011, 473, 394-397 or other types of modified sugars.

It is noted that the first reactive group may be transferred to the target site in protected form, i.e. as a functional group that can be converted into the first reactive group with removal of a protecting group, such as an acetyl. For example, thiols as the first reactive group may be transferred to the target site with an acetyl protecting group (—S—COCH$_3$) which can be readily removed to yield thiol (—SH) by treatment of modified DNA with 20% ammonia (Example 1). As the skilled person will appreciate, the purpose of the protecting group is to maintain the first reactive group until it is required to react with the second reactive group. In this regard, the second reactive group attached to the linking group can also be in protected form, with the protecting group being removed prior to reaction with the first reactive group. Suitable first and second reactive groups are shown in Table 2 below. The person skilled in the art will be aware of suitable protecting groups to be utilised with these reactive groups.

As an alternative to enzymes, chemical modification reactions can be used to derivatise the target site (Table 2), which are either nucleotide specific, or even non-specific (any nucleotide, or an abasic nucleotide, can be modified) (Hermanson, G. T. Bioconjugate techniques, Academic Press, 1996, p. 640-671; Nielsen, *J. Mol. Recognition,* 1990, 3, 2-25; Kubo et al., *Biochemistry,* 1992, 31, 3703; Lilley. *Methods Enzymol.,* 1992, 212, 133-139). In particular, chemical modification can be performed with compounds comprising the reactive groups shown below in Table 2.

TABLE 1

Reactive groups/reagents for covalent modification of nucleic acids

| NA reactive group | Target position in nucleotide | Reactive group (X) attached |
| --- | --- | --- |
| Cis-platinum | N7-guanine | terminal alkyne, |
| Alkyl-mercury(II) | C5-cytosine/uracil | amine, maleimide |
| Bisulfite/amine or hydrazide | N4-cytosine | alkyne, amine, hydrazide, azide |
| Hydrazide, hydroxylamine | Abasic sites (aldehyde groups) | alkyne, hydrazide, hydroxylamine, amine, thiol |
| N-Bromosuccinimide/ primary amine | C8-guanine | alkyne, amine, azide, protected thiol |
| Metaperiodate/ hydrazide, hydroxylamine | glucosylated nucleotide | hydrazide, hydroxylamine, amine, azide |
| Arylazide, diazirine (photoactive) | amino groups in nucleobases | alkyne, hydrazide, NHS, aldehyde, azide, pyridyldisulfide |
| Carbodiimide | phosphate groups | alkyne, azide, carbodiimide |
| Iodoacetamide, maleimide | thiolated nucleobases (in RNA) | maleimide, alkyne, azide |

The frequency of derivatisation using chemical modification methods can be controlled using different reagent concentrations and reaction times, with "single-hit" conditions being achieved with low reagent concentrations and short reaction times.

In the second step, of the two step procedure for the forming of the covalent linkage between the linking unit and the primer, the target site derivatized with the first reactive group is reacted with a second reactive group attached to the linking unit under conditions to allow this reaction. Accordingly, the first reactive group and second reactive group must be capable of reacting with each other. Suitable reactive group pairs and the resulting covalent linkages according to the invention are shown below in Table 2. The person skilled in the art will be aware of suitable conditions for these reactions. For example, conditions are described and relevant literature references given in WO2006/108678.

TABLE 2

Reactive groups may comprise a variety of combinations

| First (X) or second (Y) reactive group | First (X) or second (Y) reactive group | Covalent linkage |
| --- | --- | --- |
| Primary amine | N-hydroxysuccinimidyl ester | amide |
| Primary amine | thioester | amide |
| Primary amine | isothiocyanate | thioureas |
| Primary amine | imidoester | imidate |
| Primary amine | aldehyde, ketone | imine (amine after reduction) |
| Thiol | maleimide | thioether |
| Thiol | haloacetamide | thioether |
| Thiol | aziridine | thioether |
| Thiol | thiol | disulfide |
| Thiol | pyridyldisulfide | disulfide |
| 1,2-Diol | arylboronic acid | cyclic ester |
| Hydrazine | aldehyde, ketone | hydrazone |
| Hydroxylamine | aldehyde, ketone | oxime |
| 1,2-Aminothiol | aldehyde, ketone | thiazolidine |
| 1,2-Aminothiol | thioester | amide |
| Azide | alkyne | 1,2,3-triazole |
| Azide | phosphane ester | amide |
| Diene | dienophile | cyclohexene |
| Terminal alkyne | arylhalide | arylalkyne |
| Arylhalide | arylboronic acid | biaryl |
| Terminal silylalkyne | terminal haloalkyne | diyne |

As indicated above, a one-step procedure can be used instead of a two-step procedure to covalently attach the linking unit to the target site. Again, these methods can be performed using enzymatic or chemical modification of the target site. In an example of a one-step procedure a methyltransferase enzyme using as a cofactor a synthetic SAM comprising the linking group, can be used to transfer the linking group from the cofactor directly to the target site. In such a method the covalent linkage between the template nucleic acid sequence and the linking unit is formed by contacting the target site with a cofactor to which the linking unit is conjugated and an enzyme, under conditions that allow the enzyme to transfer the linking unit from the cofactor to the target site. In particular, the groups listed above in Table 2 can be used to conjugate the linking unit to an enzyme cofactor, e.g. to conjugate the linking unit to the AdoMet cofactor of the methyltransferase enzymes.

The choice of enzyme or chemical modification method depends on the aim of the method, the nature of the target site and the desired derivatisation. The term "target site" in the present invention is used to refer both to a site to which a linking unit can be covalently attached, and to a site to which the linking unit is attached. The target site is a region in the template nucleic acid sequence comprising or consisting essentially of a nucleotide or an abasic nucleotide which is available for derivatisation with a first reactive group, is derivatised with a first reactive group, or to which the linking unit is covalently attached. In some embodiments the target site comprises a recognition site for an enzyme, preferably a methyltransferase enzyme.

In some embodiments, the method of the present invention can be used to determine whether or not the target site is present or available for derivatisation in a particular nucleic acid sequence. If the target site is present and available for derivatisation the nucleic acid sequence can be used as a template for polymerisation. If the target site is not present, or if is not available for derivatisation, the nucleic acid sequence does not become a template for polymerisation. Accordingly, the absence of a produced (i.e. polymerised) nucleic acid molecule can be used to determine the absence or non-availability of the target site. In particular, the target site may not be present due to the presence or absence of a modification on the nucleotide which prevents its derivatisation. Alternatively, the target site may not be available for derivatisation due to being blocked by bound proteins, etc.

In some embodiments, the target site comprises a plurality of nucleotides of the template nucleic acid sequence. The target site may comprise any nucleotide sequence 2-8 nucleotides long. More preferably, the target site may comprise CG, CCGG, GCGC, GCG, or TCGA.

In some embodiments the target site may simply be a single nucleotide modified with a hydroxymethyl group. The hydroxymethyl group may be a naturally occurring modification of the nucleic acid sequence. Preferably, the nucleotide which is modified with a hydroxymethyl group is cytosine. Most preferably, the cytosine is modified with the hydroxymethyl group at the 5 position (5-hydroxymethyl cytosine, hmC). In some circumstances the nucleotide which is modified is uracil. 5-hydroxymethyluracil is also known in certain organisms (*Trypanosome brucei*, bacteriophages Gommers-Ampt and Borst, 1995, FASEB J. 9:1034-1042 and even in humans (Djuric et al., 1996, Cancer, 77:691-696).

In particular, in a preferred embodiment the present invention provides a method for determining the presence or availability of a target site comprising a nucleotide within a template nucleic acid sequence, which method comprises:

(a) contacting the template nucleic acid sequence with a compound comprising a first reactive group and an enzyme, wherein the enzyme is capable of transferring the first reactive group, or a part of the compound comprising the first reactive group, onto the nucleotide;

(b) contacting the nucleic acid sequence with a second reactive group attached to a linking unit, optionally wherein the linking unit is attached to a primer under conditions that allow the first reactive group to react with the second reactive group to form a covalent linkage;

(c) optionally, where the primer is not attached to the linking unit in step (b), binding a primer to the linking unit;

(d) contacting the nucleic acid sequence and the primer with a nucleic acid polymerase under conditions which allow the nucleic acid polymerase to produce a nucleic acid molecule from the primer based on the template nucleic acid sequence; and (e) detecting the presence or absence of the produced nucleic acid molecule so as to determine the presence or availability of the target site.

Optionally steps (a) and (b) are combined in a single step comprising contacting the template nucleic acid sequence with a cofactor comprising the linking unit and an enzyme under conditions which allow the enzyme to transfer the linking unit from the cofactor onto the nucleotide.

Preferably the nucleotide is a cytosine. Accordingly, in a further preferred embodiment the present invention provides a template nucleic acid sequence attached to a linking unit and a primer, wherein the linking unit is attached to a target site in the template nucleic acid sequence with a covalent linkage, and wherein the target site comprises a cytosine to which the linking unit is attached. Preferably the primer is base paired to an oligonucleotide strand within the linking unit, and the oligonucleotide strand is covalently attached to the remainder of the linking unit. Still more preferably the primer comprises a G residue, a C, or a GC or CG at its 3' end.

The methods of the invention described herein (and steps (d) and (e) above) may further comprise determining the sequence of the produced polynucleotide strand, mapping the 5'-sequence immediately following the primer to its genetic locus, and/or determining the size of the produced polynucleotide strand(s) by amplification with an external locus primer and a tag-specific primer and further mapping modifiable target sites relative the locus primer.

Suitable methods of sequencing the produced nucleic acid molecules are well known to a person skilled in this art. For example, a nucleic acid fragment may be sequenced using any appropriate technique already established or currently in use, such as Maxam-Gilbert, Sanger, pyrosequencing, sequencing-by-synthesis, sequencing-by-ligation, single-molecule real-time sequencing and mass spectrometry.

Alternatively, the methods of the invention can comprise a single step of DNA strand synthesis and sequencing (Sequencing by synthesis). This step may be performed with single DNA molecules using methods described in prior art (Harris et al., 2008, *Science* 320, 106; Eid et al., 2009, *Science* 323:133-138).

Further the methods may comprise analysis of the nucleic acid fragments using DNA microarrays.

Methods of amplifying nucleic acid fragments are well known to a person skilled in this art. The amplification is preferably achieved by means of a polymerase chain reaction (PCR) or any isothermal DNA amplification method including but not limited to RCA, NASBA, LAMP, HDA, ICAN, NEAR and, EXPAR. The nucleic acid fragments may be quantified using a quantitative polymerase chain reaction or microarray analysis.

In particular, PCR amplification with a random primer and a tag-specific primer can be used to amplify all polynucleotide products produced from the tagged primer. Most favorably, the tag primer can be similar to or match the sequence of that used for attaching and priming sequencing reaction in a commercial sequencing machine. (This permits direct hybridization of tag-primed products for sequencing. Other fragments produced between two random primers would not be sequenced).

In particular, locus specific probes can be utilised to amplify particular fragments from the produced nucleic acid molecule in order to characterize the sequence modification. This step can also comprise determining the size of the produced polynucleotide strand(s) by amplification with an external locus primer and a tag-specific primer and further comprise mapping of unmodified/accessible target sites relative the locus primer.

Further to amplification PCR fragments may optionally be cleaved with restriction enzymes and then analysed by gel electrophoresis to reveal the distance between the probe and the target size thereby permitting its mapping in a DNA molecule of known nucleotide sequence. Analysis of amplification patterns can also be performed by sequencing or DNA microarrays.

The nucleic acid polymerase referred to herein is an enzyme that extends a nucleic acid strand from a primer. In particular, the polymerase may be a DNA-dependent DNA polymerase, or an RNA-dependent DNA polymerase such as reverse transcriptase. Examples of suitable nucleic acid polymerases for use in the methods of the invention are TaqI or PfuI polymerase.

Conditions which allow the polymerase to utilise the primer to polymerize a nucleic acid molecule are known in the art. In particular, where the template nucleic acid sequence is double-stranded DNA, a melting step utilised to physically separate the lower strand, and then the temperature is dropped such that the covalently linked primer can come into a position to start the strand synthesis. Although the hybridization process in the present invention is different from that in the prior art, as it does not involve extended base pair formation across the full length of the primer, in the present invention the interaction of the 3' end of the primer with the template may be achieved under similar conditions to those described in the prior art. Preferably this enables interaction of the 3' end of the primer with one or more nucleotides in the template nucleic acid sequence. The polymerase is able to produce a new polynucleotide strand from the tethered primer starting at the site of the derivatized nucleotide or adjacent thereto. In particular, incoming nucleotides are added at the 3'OH terminus of the primer. The first one or two nucleotides may not necessarily require correct base pairing. However, further strand extension is template dependent such that the nucleic acid polymerase synthesises a new nucleic acid molecule based on (complementary to) the template nucleic acid sequence.

In a further aspect, the present invention provides a kit for use in producing a nucleic acid molecule comprising:

(a) an enzyme capable of covalent derivatization of a nucleotide in a nucleic acid sequence with a first reactive group;
(b) a compound comprising the first reactive group;
(c) a linking unit attached to a second reactive group; and
(d) optionally a nucleic acid polymerase enzyme.

Each element of the kit is in a separate container. The kit may optionally further comprises instructions for using the components of the kit in order to detect a target site within a nucleic acid. The instructions are provided on an appropriate medium, for example paper or an electronic data carrier.

The description herein regarding the methods of the present invention also applies to the elements of the kit of the invention. In particular, in the kit the linking unit may be attached to a primer, or alternatively the primer may be provided as part of the kit in a separate container. Where the primer is provided with the linking unit it can be covalently or non-covalently bound to the linking unit. In the case of the latter, the linking unit may comprise a nucleic acid strand to which the primer is capable of base pairing.

Further, the first and/or second reactive groups may be in protected form, as described above, to allow for their stable storage.

The kit may further comprise an affinity binding group attached to the primer and/or the linking unit. The kit may also further comprise reagents for amplifying and/or detecting nucleic acid fragments, such as nucleotides (dNTPs), buffers, restriction enzymes, sequence specific primers, and adaptors.

Where a polymerase is present, this may be a variant, engineered such that it is suited for the specific purpose, e.g. efficient strand extension from a primer attached to a linking unit which is covalently linked to a target site in the template nucleic acid sequence, in a similar manner to which polymerases are engineered for higher processivity, better uptake of nucleotide analogues, etc. The polymerase may be provided prearranged in a particular concentration and buffer suitable for use in the methods of the present invention.

In further aspects the present invention provides the use of a method of the first aspect of the invention to determine the presence or availability of a target site in a nucleic acid molecule, and the use of a linking unit attached to a primer for priming a nucleic acid polymerase reaction, wherein the linking unit is to be attached to a target site in a nucleic acid sequence with a covalent linkage. Still further the present invention provides a template nucleic acid sequence attached to a linking unit and a primer, wherein the linking unit is attached to a target site in the template nucleic acid sequence with a covalent linkage. The preferred embodiments described above for the invention apply to these aspects.

FIG. 1 shows a general scheme for mapping of covalently tagged target sites in DNA.

FIG. 2 shows a scheme for whole genome mapping of modifiable CG target sites (3' polyA tail; AAAAAAAAAA (SEQ ID NO: 18) and polyd(T) primer; TTTTTTTTTTTTTT (SEQ ID NO: 19)).

FIG. 3 shows a scheme for locus-specific mapping of unmodified target sites in DNA by sizing PCR products.

FIG. 4 shows a strategy for sequence mapping of covalently tagged GCGC sites in a DNA fragment (LnkUnit-tethered DNA; TTTTTTTTTCTCCC (SEQ ID NO:20).

Figure 5:
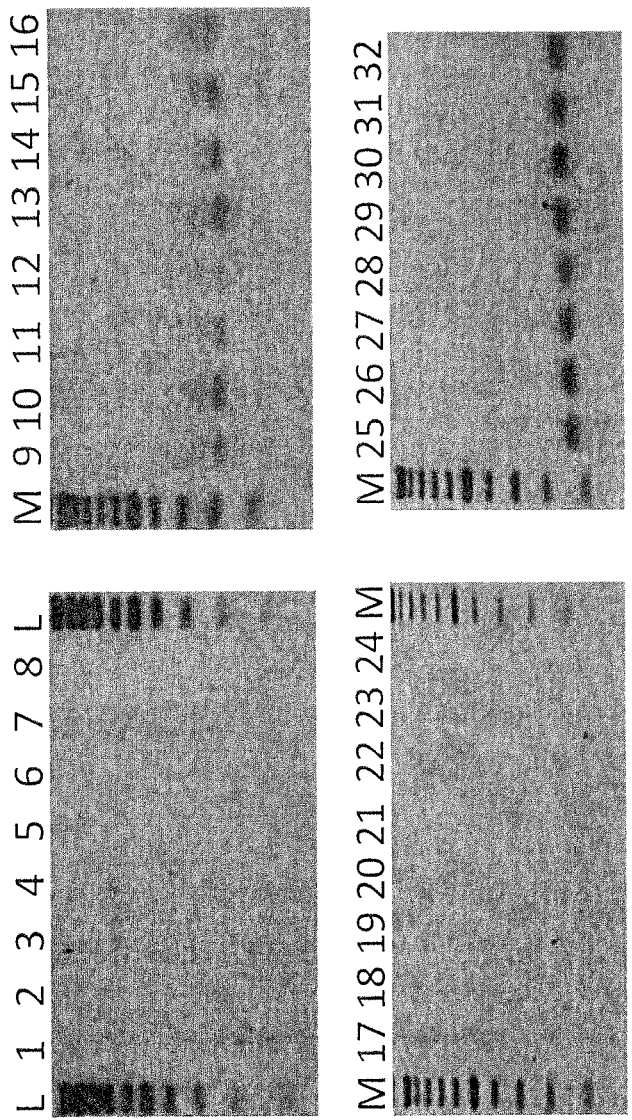
FIG. 5 shows production of a new polynucleotide strand using DNA polymerase reaction primed at an unmodified target site in a DNA fragment.

FIG. 5 shows production of a new polynucleotide strand using DNA polymerase reaction primed at an unmodified target site in a DNA fragment. The 267pBR DNA fragment was covalently derivatized with the 6-(acetylmercapto) hexyn-2-yl group at a single GCGC target site by mTAG modification with M.HhaI (variant Q82A/Y254S/N304A) and AdoS(Ac) cofactor followed by removal of the protecting acetyl group by ammonia treatment. The DNA was then further conjugated to a priming adapter (maleimide-containing oligonucleotide), which permits adapter-directed hybridization of a variety of priming oligonucleotides to the DNA fragment. The production of a new polynucleotide strand with PfuI or TaqI DNA polymerase primed by the tethered oligonucleotide was achieved by performing four re-annealing and extension cycles (95° C./1 min, 45° C./1 min, 72° C./1 min) in 30 μl of PfuI buffer with MgSO$_4$ containing 1 u. of PfuI DNA polymerase, 0.2 mM dNTP (Fermentas), 0.5 μM of tag-specific priming oligodeoxynucleotide (GGGAGA$_{14}$ (SEQ ID NO:1) lanes 1, 9, 17, 25; GGGAGA$_{15}$ (SEQ ID NO:2) lanes 2, 10, 18, 26; GGGAGA$_{15}$G (SEQ ID NO:3) lanes 3, 11, 19, 27; GGGAGA$_{15}$C (SEQ ID NO:4) lanes 4, 12, 20, 28; GGGAGA$_{15}$NCG (SEQ ID NO:5) lanes 5, 13, 21, 29; GGGAGA$_{16}$ (SEQ ID NO:6) lanes 6, 14, 22, 30; GGGAGA$_{16}$C (SEQ ID NO:7) lanes 7, 15, 23, 31; GGGAGA$_{15}$IC (SEQ ID NO:8) lanes 8, 16, 24, 32); and template DNA (267pBR DNA, lanes 1-8, 17-24; 267pBR-amT1, lanes 9-16, 25-32).

The efficiency and specificity of tether-primed synthesis was estimated by performing 25 PCR cycles in the presence of a tag-specific primer and a locus-specific primer oligonucleotide (pBR-164dir or pBR-99rev) that is complementary to one of the terminus of the 267pBR DNA fragment. PCR analysis of the primed polynucleotide strands was performed by combining 3 μl of the reaction samples, 1.5 μl of a 10 μM tag-specific primer and 1.5 μl of a 10 μM terminal primer in 25 μl of PfuI buffer containing PfuI DNA polymerase (0.05 u/μl) and 0.2 mM dNTPs. Terminal primers were used as follows: pBR-99rev (lanes 1-16), pBR-164dir (lanes 17-32). 25 cycles (95° C./30 s, 55° C./30 s, 72° C./30 s) of PCR were carried out. Reaction products were analysed by agarose gel electrophoresis (lanes 1-41); M—DNA Ladder Mix (#SM1173, Fermentas), L—100 bp DNA Ladder (#SM1143, Fermentas).

Appearance of intense bands of a correct size about 122 bp and 187 bp in lanes 9-16 and 25-32 indicates efficient priming of strand synthesis at or around the target site. This synthesis is tag-dependent since control reactions with covalently unmodified DNA (lanes 1-8, 17-24) give no such PCR products.

Figure 6:
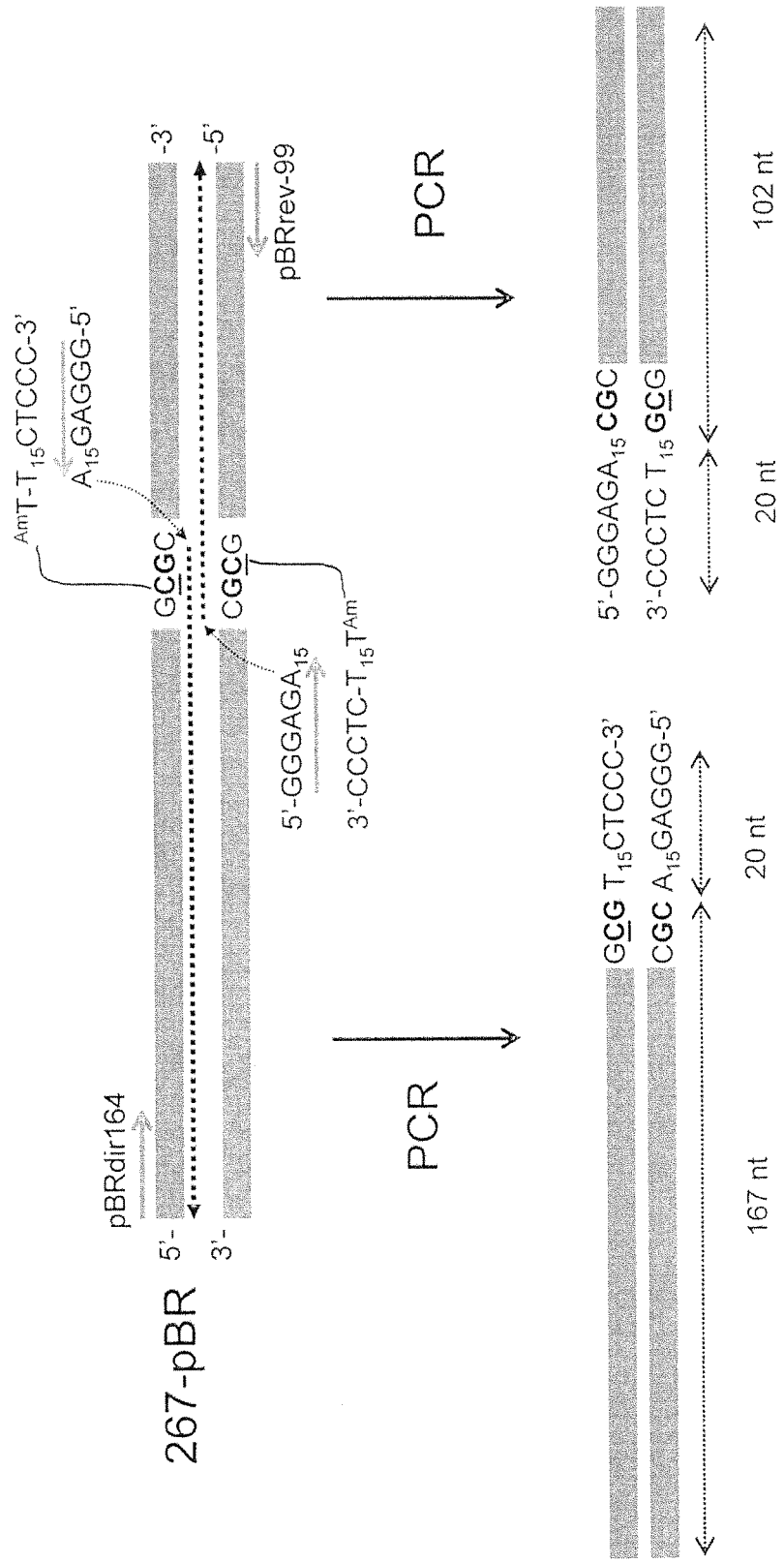
FIG. 6 shows theoretical PCR products derived from the 267pBR template primed at a target HhaI site and a terminal locus-specific primer (Linked primer=SEQ ID NO: 21).

FIG. 6 shows theoretical PCR products derived from the 267pBR template primed at a target HhaI site and a terminal locus-specific primer (Linked primer=TTTTTTTTTTTTTTTCTCCC (SEQ ID NO: 21)).

Figure 7:
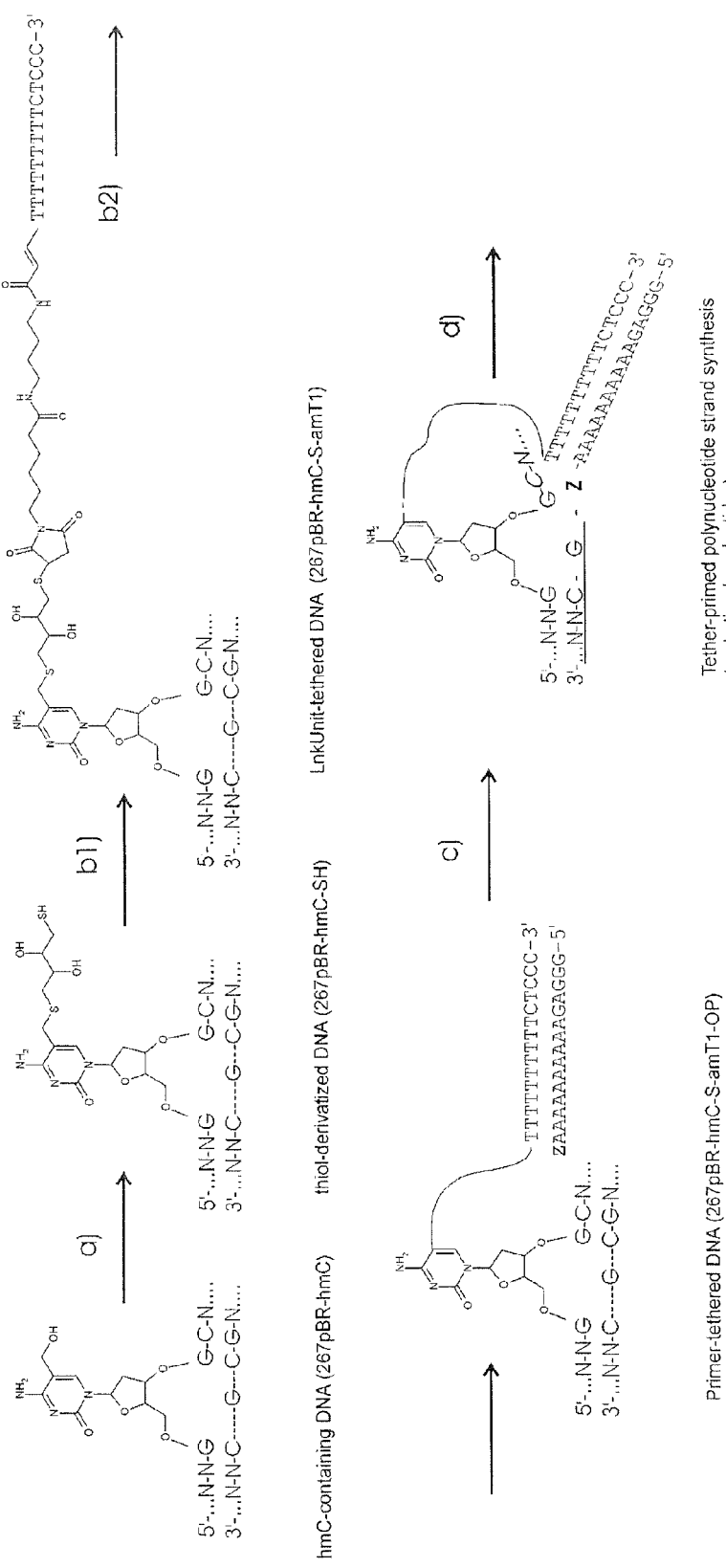
FIG. 7 shows strategy for sequence mapping of covalently tagged 5-hydroxymethylated GCGC sites (GhmCGC) in a DNA fragment (LnkUnit-tethered DNA (SEQ ID NO:20).

FIG. 7 shows strategy for sequence mapping of covalently tagged 5-hydroxymethylated GCGC sites (GhmCGC) in a DNA fragment (LnkUnit-tethered DNA (SEQ ID NO:20).

Figure 8:
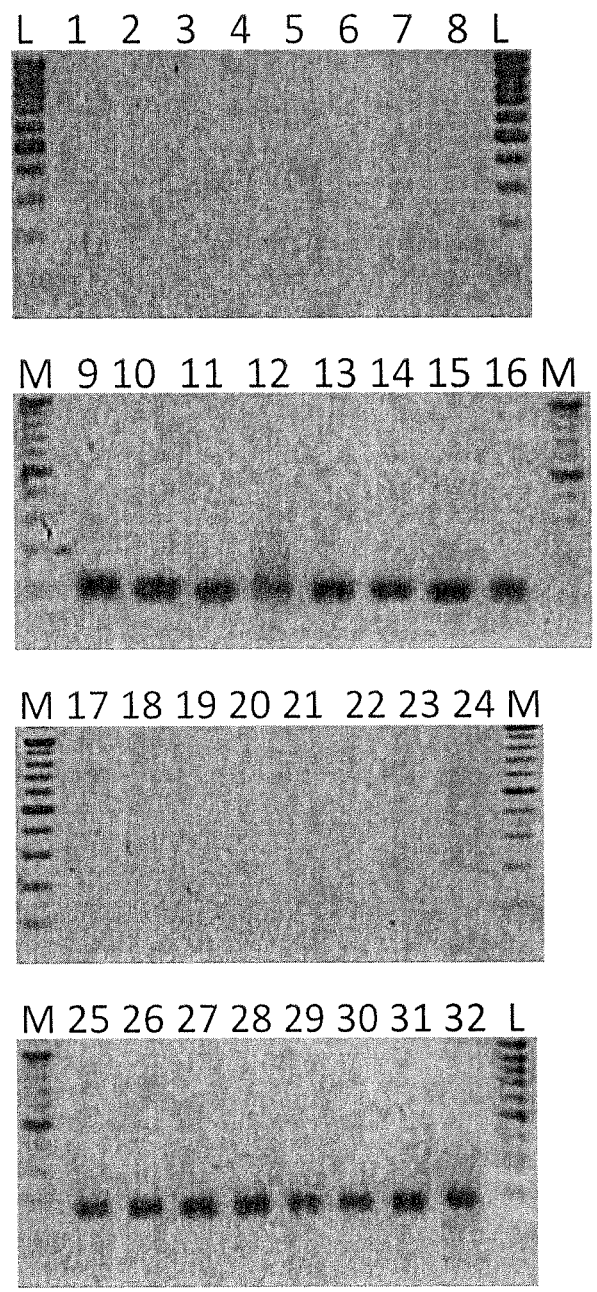
FIG. 8 shows production of a new polynucleotide strand using DNA polymerase reaction primed at a hydroxymethylcytosine-containing target site in a DNA fragment.

FIG. 8 shows production of a new polynucleotide strand using DNA polymerase reaction primed at a hydroxymethylcytosine-containing target site in a DNA fragment.

DNA fragment 267pBR containing a hmC-modified GCGC target site was covalently derivatized with the 4-mercapto-(2,3-dihydroxy)-butylthio group by M.HhaI-directed reaction with 1,4-dithiothreitol. The DNA was then conjugated to a priming adapter (maleimide-containing oligonucleotide [maleimide-aminoT]-T$_{14}$-CTCCC-3') (SEQ ID NO:9), which permits adapter-directed hybridization of a variety of priming oligonucleotides to the DNA fragment. The production of a new polynucleotide strand with PfuI or TaqI DNA polymerase primed by the tagged oligonucleotide was achieved by performing four re-annealing and extension cycles (95° C./1 min, 45° C./1 min, 72° C./1 min) in 30 µl PfuI buffer with MgSO$_4$ containing 1 u. PfuI DNA polymerase, 0.2 mM dNTP (Fermentas), 0.5 µM of tag-specific priming oligodeoxynucleotide (GGGAGA$_{14}$ (SEQ ID NO:1) lanes 1, 9, 17, 25; GGGAGA$_{15}$ (SEQ ID NO:2) lanes 2, 10, 18, 26; GGGAGA$_{15}$G (SEQ ID NO:3) lanes 3, 11, 19, 27; GGGAGA$_{15}$C (SEQ ID NO:4) lanes 4, 12, 20, 28; GGGAGA$_{15}$NCG (SEQ ID NO:5) lanes 5, 13, 21, 29; GGGAGA$_{16}$, (SEQ ID NO:6) lanes 6, 14, 22, 30; GGGAGA$_{16}$C (SEQ ID NO:7) lanes 7, 15, 23, 31; GGGAGA$_{15}$IC (SEQ ID NO:8) lanes 8, 16, 24, 32), and template DNA (267pBR DNA, lanes 1-8, 17-24; 267pBR-hmC-AmT1, lanes 9-16, 25-32).

The efficiency and specificity of tag-primed synthesis was estimated by performing further 25 PCR cycles in the presence of a tag-specific primer and the locus-specific primer oligonucleotide (pBR-164dir or pBR-99rev). PCR analysis of the primed polynucleotide strands was performed by combining 3 µl of the reaction samples, 1.5 µl of a 10 µM tag-specific primer and 1.5 µl of a 10 µM terminal primer in 25 µl of the PfuI buffer containing PfuI DNA polymerase (0.05 u/µl) and 0.2 mM dNTPs. Terminal primers were used as follows: pBR-99rev (lanes 1-16), pBR-164dir (lanes 17-32). 35 cycles (95° C./30 s, 55° C./30 s, 72° C./30 s) of PCR were carried out. Reaction products were analysed by agarose gel electrophoresis (lanes 1-41); M—DNA Ladder Mix, L—100 bp DNA Ladder (Fermentas).

Appearance of intense bands of approximately 122 bp and 187 bp long in lanes 9-16 and 25-32 indicates efficient priming of strand synthesis at or around the target site. This synthesis is tag-dependent since control reactions with covalently unmodified DNA (lanes 1-8, 17-24) give no such PCR products.

Figure 9:
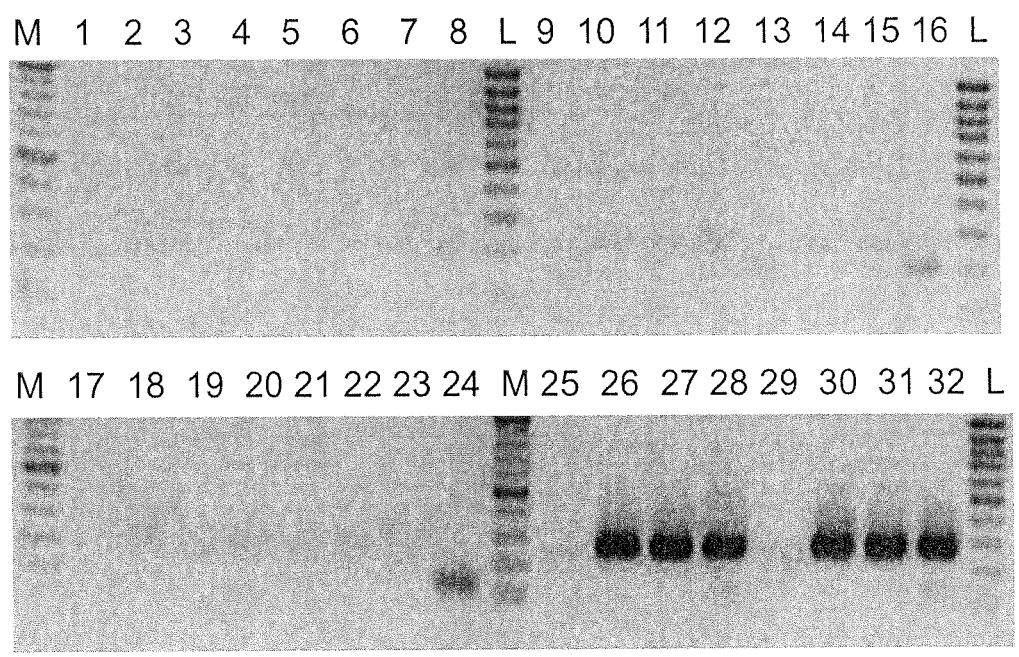
FIG. 9 shows control reactions of Polymerase site-specific priming reaction.

FIG. 9 shows control reactions of polymerase site-specific priming reaction. Reactions were performed under the following conditions: template 0.05 µM, tagged primer GGGAGA$_{15}$-NCG (SEQ ID NO:5) 0.5 µM, PfuI DNA polymerase 0.05 u/µl, PfuI buffer with MgSO$_4$, dNTP 0.2 mM (Fermentas). Reaction volume was 30 µl, initial denaturation step 95° C. 2 min, three cycles (95° C. 2 min, 45° C. 1 min, 72° C. 1 min). Following templates were used: no template—lanes 1, 5, 9, 13, 17, 21, 25, 29; 267pBR fragment, gel-extracted with silica kit (Fermentas)—lanes 2, 6, 10, 14, 18, 22, 26, 30; 267pBR fragment, purified with Qiaquick kit (Qiagen)—lanes 3, 7, 11, 15, 19, 23, 27, 31; 267pBR—amT1 conjugate—lanes 4, 8, 12, 16, 20, 24, 28, 32. Amplification reaction was performed by mixing reaction solution from the priming stage with the following mix: PfuI DNA polymerase (2 u), dNTP mix (0.2 mM each), 1× Pfu buffer with MgSO$_4$ (Fermentas), locus-specific primer (0.5 µM). 25 thermal cycles were applied (95° C./1 min, 45° C./1 min, 72° C./1 min). The primers were used as follows: locus primer—none (lanes 1-8); locus primer pBR-164dir (lanes 9-16); locus primer pBR-99rev (lanes 17-24); locus primer both pBR-164dir and pBR-99rev (lanes 25-32). Products were analyzed by agarose gel-electrophoresis. M—DNA Ladder Mix, L—100 bp DNA Ladder (Fermentas).

Figure 10:
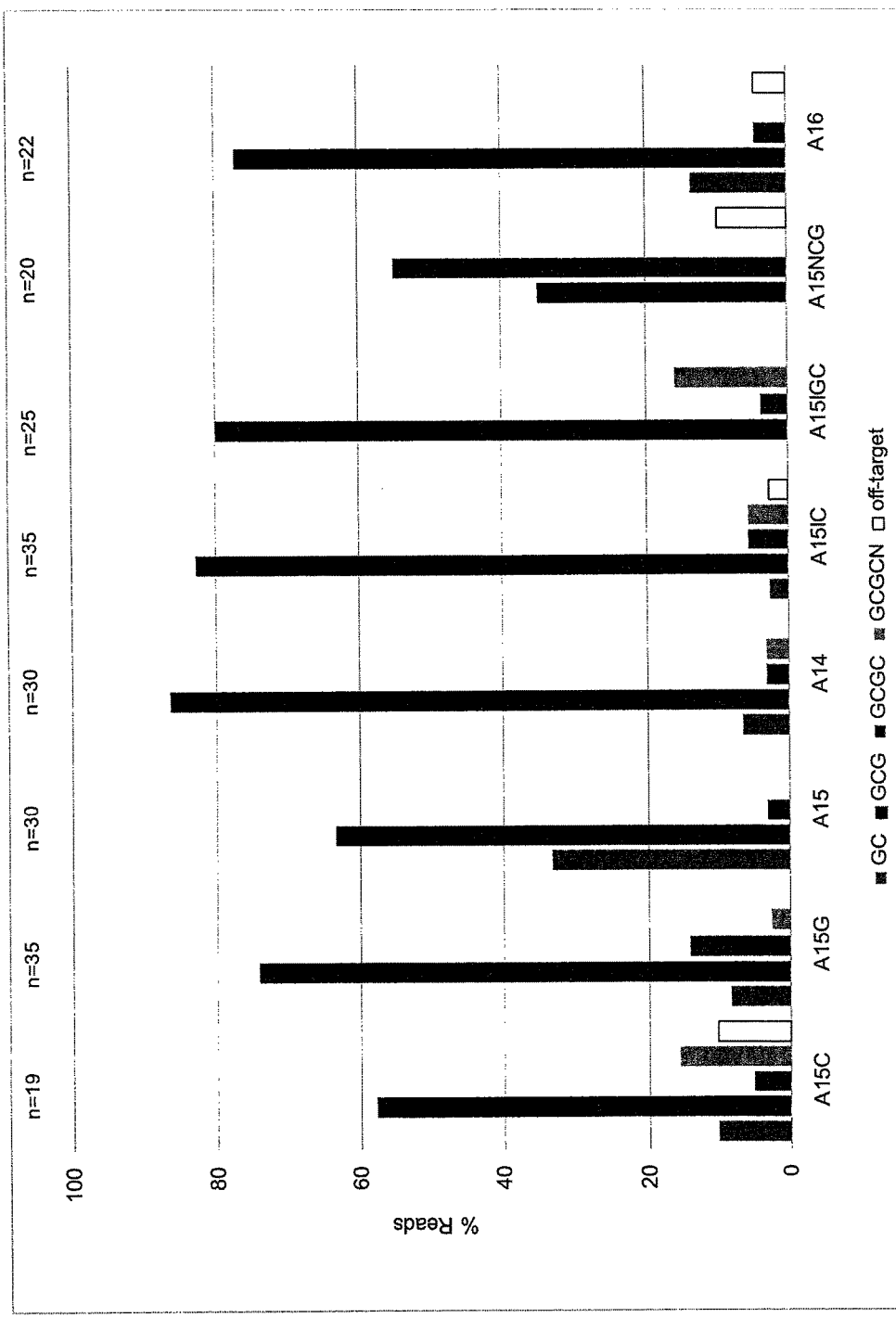
FIG. 10 shows sequencing results of clones obtained from covalently tagged GCGC target sites with thiol groups as described in Example 1.

FIG. 10 shows sequencing results of clones obtained from covalently tagged GCGC target sites with thiol groups as described in Example 1. PfuI polymerase read start positions obtained with different tag priming oligonucleotides are shown as a fraction of total reads. Annealed oligonucleotide primers are of a general sequence GGGAGA$_N$Z (abbreviated ANZ).

Figure 11:
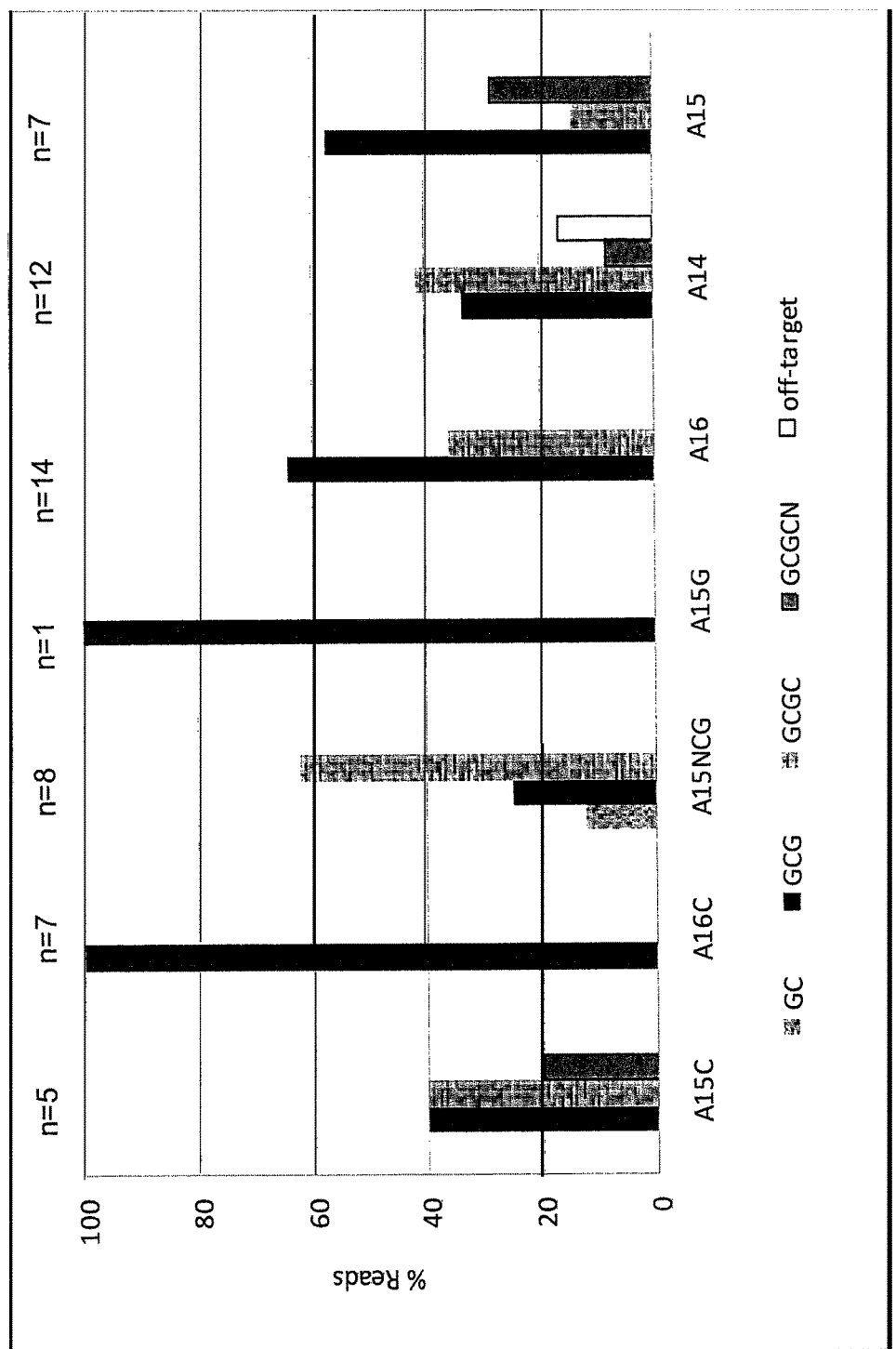
FIG. 11 shows sequencing results of clones obtained from covalently tagged 5-hydroxymethylated GCGC target sites (GhmCGC) in a DNA fragment as described in Example 2.

FIG. 11 shows sequencing results of clones obtained from covalently tagged 5-hydroxymethylated GCGC target sites (GhmCGC) in a DNA fragment as described in Example 2. PfuI polymerase read start positions obtained with different tag priming oligonucleotides are shown as a fraction of total reads. Annealed oligonucleotide primers are of a general sequence GGGAGA$_N$Z (abbreviated ANZ).

Figure 12:
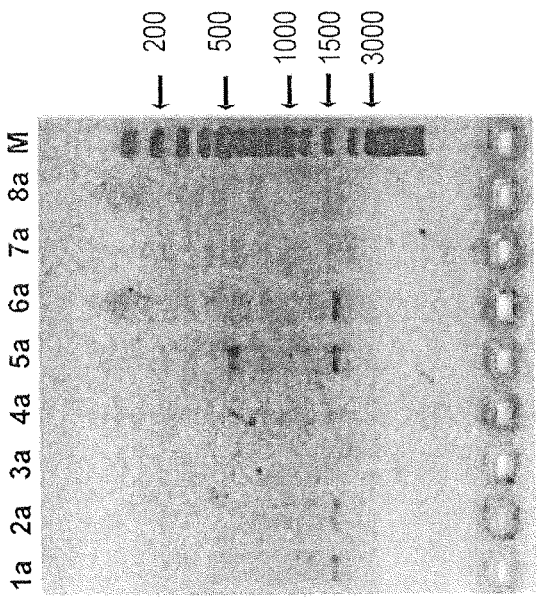
FIG. 12 shows production of a new polynucleotide strand using DNA polymerase reaction primed at multiple unmodified target sites in a plasmid DNA.
Figure 12:
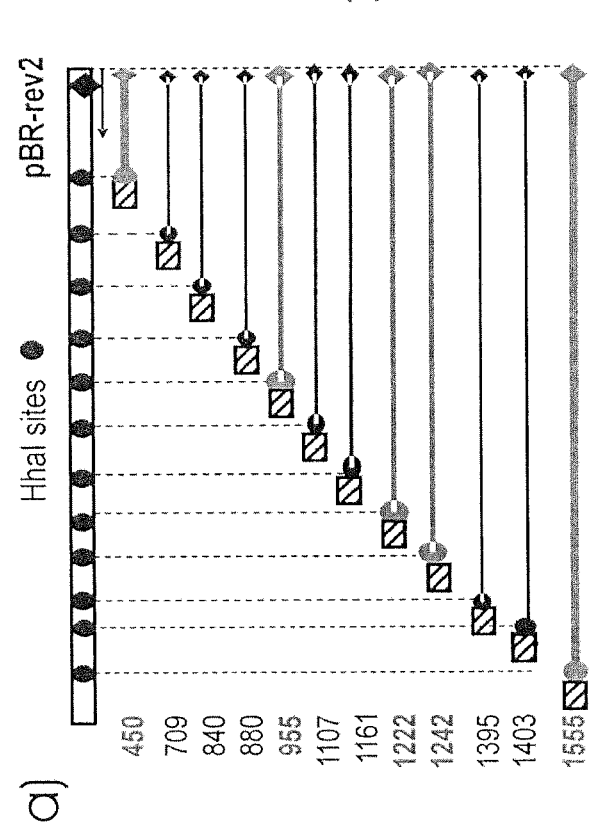
Figure 12:
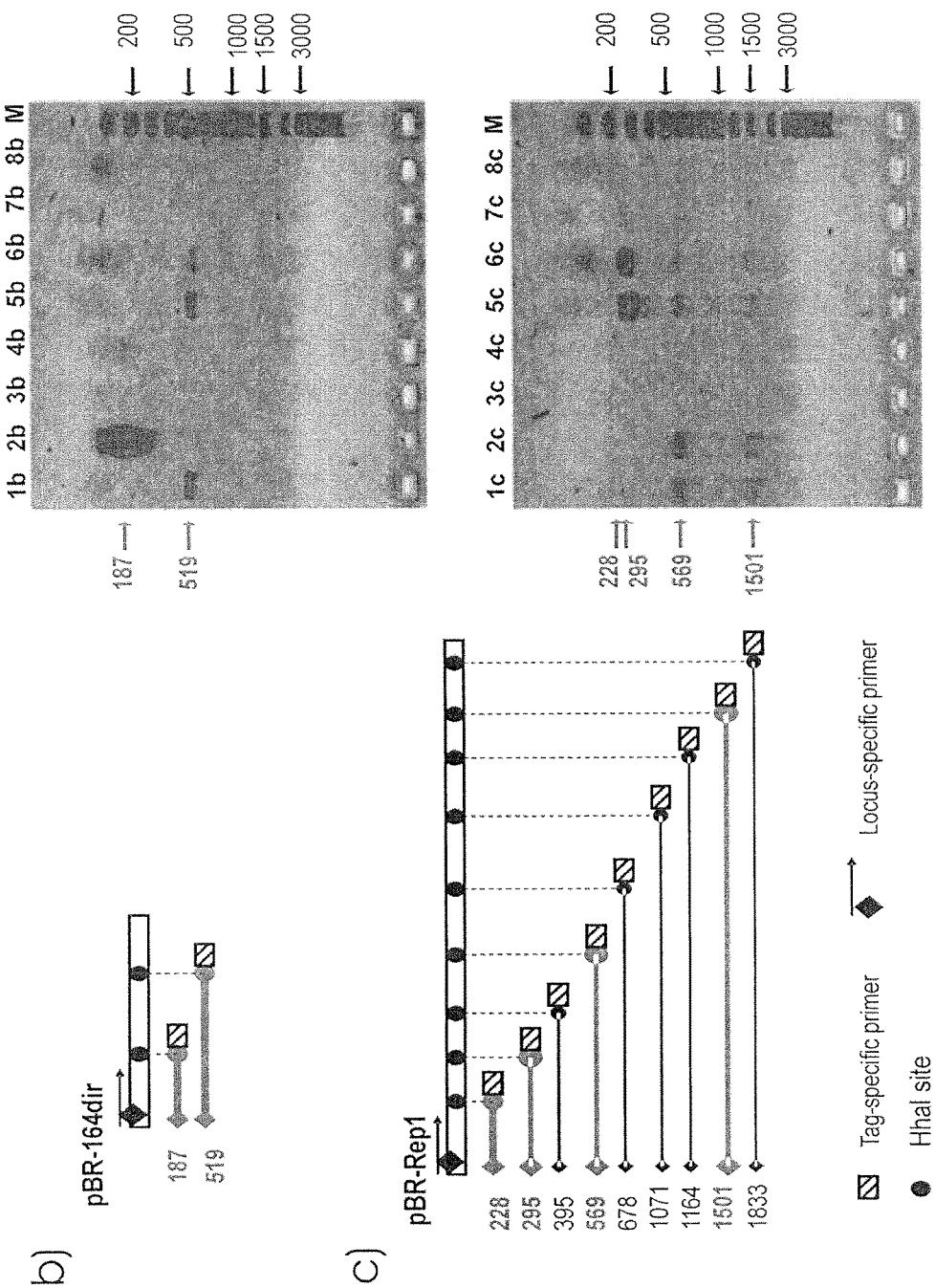

FIG. 12 shows production of a new polynucleotide strand using DNA polymerase reaction primed at multiple unmodified target sites in a plasmid DNA. Left, predicted PCR fragments from primer-tagged HhaI sites in pBR322 plasmid DNA using three locus-specific probes primers: (a) pBR-rev2 [1639-1620, lower strand]; (b) pBR-164dir [3760-3782, upper strand]; (c) pBR-Rep1 [2446-2466, upper strand]. Right, agarose gel electrophoretic analysis of produced PCR fragments. Lanes 1a, 1b, 1c contain pBR322-SH, tag primer: GGGAGA$_{14}$ (SEQ ID NO:1); Lanes 2a, 2b, 2c contain pBR322-SH, tag primer: GGGAGA$_{16}$C (SEQ ID NO:7); Lanes 3a, 3b, 3c contain pBR322 (control), tag primer: GGGAGA$_{14}$ (SEQ ID NO:1); Lanes 4a, 4b, 4c contain pBR322, tag primer: GGGAGA$_{16}$C (SEQ ID NO:7); Lanes 5a, 5b, 5c contain pBR322-NH2, tag primer: oligoM2; Lanes 6a, 6b, 6c contain pBR322-NH2, tag primer: oligoM2/oligoM3; Lanes 7a, 7b, 7c contain pBR322, tag primer: oligoM2; Lanes 8a, 8b, 8c contain pBR322, tag primer: oligoM2/oligoM3; Lanes 1a-8a contain locus primer pBR-rev2; Lanes 1b-8b contain locus primer pBR-164dir; Lanes 1c-8c contain locus primer pBR-Rep1; M,—DNA Ladder Mix (Fermentas).

The present invention will now be described in further detail, by way of example only, with reference to the following Examples and related Figures.

EXAMPLES

Example 1. Sequence Mapping of Covalently Tagged Unmodified GCGC Target Sites in a DNA Fragment A 267 bp DNA fragment (267pBR) produced by PCR amplification was used as a model substrate (FIG. 12), although it is clear any other DNA fragment of any origin is suitable. The DNA fragment was obtained by PCR using the pBR322 plasmid as a template, pBR-164dir and pBR-99rev oligonucleotides each 0.5 µM concentration, by using standard PCR protocol (Fermentas catalogue 2010/2011).

a) Covalent Tagging of GCGC Target Sites with Thiol Groups (Preparation of a Site-Specifically Thiol-Derivatized DNA Fragment)

Covalent tagging with thiol groups of GCGC target sites in the 267pBR fragment was performed using mTAG approach (Lukinavičius et al., 2007). 267pBR DNA (final concentration 2.5 µM) was incubated with the HhaI DNA methyltransferase (variant Q82A/Y254S/N304A) (5 µM) and AdoS(Ac) cofactor (90 µM) for 2 hours at 37° C. in MOPS pH 7.4 buffer. After modification, the obtained 267pBR-S(Ac) fragment was incubated with ammonium hydroxide about 10%, evaporated to dryness in a vacuum concentrator, redissolved in deionised water ethanol precipitated and again redissolved in deionised water.

b) Tethering of a Linking Unit to a Site-Specifically Derivatized DNA Fragment (X-Y Coupling)

Maleimide-derivatized priming adapter (AmT1-maleimide) was prepared from a synthetic DNA oligonucleotide containing a 5-aminoalkyl modification at its 5'-terminal thymine residue (AmT1 oligonucleotide). AmT1 oligonucleotide (400 µM) was incubated with sulfo-GMBS reagent (Pierce) overnight in 80% DMSO and PBS 1× buffer, and then purified by using Micro-Spin G-25 gel-filtration column (GE Healthcare) equilibrated with DMSO (Fluka). Reactivity of AmT1-maleimide was tested by incubating with N4v-S thiolated oligonucleotide, labeling with γ-$^{32}$P-ATP and analyzing by denaturing gel electrophoresis.

Coupling of an oligonucleotide conjugate (AmT1-Y, Y=maleimide) to a modified DNA fragment (267pBR-SH, X=thiol) was performed by combining 1 µl of 100 µM AmT1-maleimide and 9 µl of 1 µM 267pBR-SH followed by incubation for 2 hours at room temperature. The obtained 267pBR-amT1 conjugate was stored at −20° C.

c) Tether-Primed DNA Strand Synthesis in a DNA Fragment

Polymerase extension reactions were performed on the oligonucleotide-conjugated template 267pBR-amT1 using annealed oligonucleotide primers of a general sequence GGGAGA$_{14}$-Z oligodeoxyribonucleotide (Z=ANCG (SEQ ID NO:10), AIGC (SEQ ID NO:11), A (SEQ ID NO:12), AIG (SEQ ID NO:13), AIC (SEQ ID NO:14), AAIGC (SEQ ID NO:15), see Table 1) using TaqI or PfuI polymerase (Fermentas) under the following conditions: template 0.05 µM, primer 0.5 µM, total volume 30 µl, initial denaturation step 95° C. 2 min, 3 cycles (95° C./1 min, 45° C./1 min, 72° C./1 min). PCR amplification was performed by using the priming reaction (15 µl) as the template which was added to 15 µl of PCR reaction mix containing pBR-164dir or pBR-99rev oligonucleotide (0.5 µM) and performing PCR 25 cycles (95° C./1 min, 45° C./1 min, 72° C./1 min).

d) Efficiency and Size-Specificity of the Tether-Primed Extension Reaction

The effectiveness and specificity of tether-primed extension reactions with a variety of annealed priming strands and under different reaction conditions can be assessed by agarose gel electrophoresis of PCR amplification products (FIG. 5). Higher intensity of bands correlates with a higher priming efficiency, whereas uniformity of a gel band of appropriate size corresponds with the specificity of priming. PCR amplification with the pBR-164dir primer is expected to give a fragment of 187 bp, whereas PCR amplification with the pBR-99rev primer is expected to give a fragment of 122 bp (FIG. 6). Consistent with the prediction, FIG. 5 shows that a major fragment produced with the pBR-164dir primer (lanes 9-16) is slightly shorter than 200 bp, whereas a major fragment produced with the pBR-99rev primer (lanes 25-32) is slightly longer than 100 bp. The presented results thus demonstrate priming of strand synthesis at a GCGC target site in a DNA fragment.

e) Sequence Analysis of Primer Extension Products

The obtained PCR fragments were blunt-ended with T4 DNA polymerase, phosphorylated with T4 polynucleotide kinase and ligated into pUC19 vector cut with HincII and EcI136II restriction endonucleases and dephosphorylated with FastAP (enzymes and reaction conditions—Fermentas catalogue 2010/2011). E. coli ER2267 strain was transformed with ligation products under standard conditions. Clones were selected by performing in situ PCR form the bacterial colonies under standard conditions, using M13/pUC-46 and M13/pUC-46(rev) primers (Fermentas).

Selected clones were grown in LB medium, plasmid minipreps were purified with GeneJET plasmid purification kit and sequenced using M13/pUC-46(rev) primer (Fermentas). The percentage of clones with fragment starting from 5'-GCGC-3' site of 267-pBR-amT1 conjugate was about 55% using TaqI polymerase and close to 100% using PfuI polymerase.

Sequencing data for PfuI polymerase are summarized in FIG. 10. The presented data indicate that the majority of sequence reads (>90%) start at the tethering target sites, demonstrating efficient sequence mapping of a GCGC target site in a DNA fragment.

Example 2. Sequence Mapping of Covalently Tagged 5-Hydroxymethylated GCGC Target Sites in a DNA Fragment a) Covalent Tagging of 5-Hydroxymethylated GCGC Target Sites with Thiol Groups (Preparation of a Site-Specifically Thiol-Derivatized DNA Fragment)

267pBR was modified with formaldehyde and M.HhaI as described (Liutkeviciute et al., Nat. Chem. Biol. 2009, 5: 400-402) to produce DNA (267pBR-hmC) containing hmC residues at the GCGC target site. Covalent tagging of hmC-containing GCGC target sites with thiol groups was generally performed as described (Liutkeviciute et al., Angew. Chem. Int. Ed., 2011, 50, 2090-2093). 267pBR-hmC DNA (final concentration 2.5 µM) was incubated with HhaI DNA methyltransferase (variant Q82A/Y254S/N304A) (5 µM) and 1,4-dithiothreitol (25 µM) for 1 hour at 25° C. in MOPS pH 7.4 buffer, and the resulting 267pBR-hmC-SH DNA was purified using a nucleotide removal kit (Qiagen).

b) Tethering of a Linking Unit to a Site-Specifically Derivatized DNA Fragment (X-Y Coupling)

Coupling of an oligonucleotide conjugate (AmT1-maleimide, Y=maleimide) to the modified DNA fragment (267pBR-hmC-SH, X=thiol) was performed by combining 1 µl of 100 µM AmT1-maleimide and 9 µl of 1 µM 267-pBR-hmC-SH followed by incubation for 2 hours at room temperature to give 267pBR-hmC-amT1 DNA.

c) Tether-Primed DNA Strand Synthesis in a DNA Fragment

Polymerase extension reactions were performed on the oligonucleotide-conjugated template 267pBR-hmC-amT1 using annealed oligonucleotide primers of a general sequence GGGAGA$_{14}$-Z oligodeoxyribonucleotide (Z=ANCG (SEQ ID NO:10), =AIGC (SEQ ID NO:11), =A (SEQ ID NO:12), =AIG (SEQ ID NO:13), =AIC (SEQ ID NO:14), =AAIGC (SEQ ID NO:15)) using TaqI or PfuI polymerase and its buffer (Fermentas) under the following conditions: template 0.05 µM, primer 0.5 µM, total volume 30 µl, initial denaturation step 95° C. 2 min, 3 cycles (95° C./1 min, 45° C./1 min, 72° C./1 min). PCR amplification was performed by using as template priming reaction from stage 3 (15 µl) which was added to 15 µl of reaction mix containing pBR-164dir or pBR-99rev oligonucleotide (0.5 µM) and performing PCR 25 cycles (95° C./1 min, 45° C./1 min, 72° C./1 min).

d) Efficiency and Size-Specificity of the Tether-Primed Extension Reaction

The efficiency and specificity of tether-primed extension reactions with a variety of priming strands and under different reaction conditions can be assessed by agarose gel electrophoresis of PCR amplification products (FIG. 8). Higher intensity of bands correlates with a higher priming efficiency, whereas uniformity of a gel band of appropriate size corresponds with specificity of priming. PCR amplification with the locus-specific pBR-164dir primer is expected to give a fragment of 187 bp, whereas PCR amplification with the locus-specific pBR-99rev primer is expected to give a fragment of 122 bp (FIG. 6). Consistent with the prediction, FIG. 8 shows that a major fragment produced with pBR-99rev primer (lanes 9-16) is slightly longer than 100 bp and a major fragment produced with pBR-164dir primer (lanes 25-32) is slightly shorter than 200 bp. The presented results thus demonstrate priming of strand synthesis at a hmC containing target site in a DNA fragment.

e) Sequence Analysis of Primer Extension Products

The obtained PCR fragments were blunt-ended with T4 DNA polymerase, phosphorylated with T4 polynucleotide kinase and ligated into pUC19 vector cut with HincII and EcI136II restriction endonucleases and dephosphorylated with FastAP (enzymes and reaction conditions—Fermentas). E. coli ER2267 strain was transformed with ligation products under standard conditions. Clones were selected by performing in situ PCR form the bacterial colonies under standard conditions, using M13/pUC-46 and M13/pUC-46 (rev) primers (Fermentas).

Selected clones were grown in LB medium, plasmid minipreps were purified with GeneJET plasmid purification kit and sequenced using M13/pUC-46(rev) primer (Fermentas).

Sequencing data for PfuI polymerase are summarized in FIG. 11. The presented data indicate that the majority of sequence reads (>90%) start at the HhaI target site, which demonstrates efficient sequence mapping of a hydroxymethylated GCGC target site in a DNA fragment.

Example 3. Mapping of Covalently Tagged GCGC Target Sites in Plasmid DNA

Tagged target mapping was further demonstrated on pBR322 plasmid DNA (4361 bp), which contains 31 GCGC targets sites.

a) Covalent Tagging of GCGC Target Sites with Thiol or Maleimide Groups (Preparation of a Site-Specifically Derivatized Plasmid DNA)

Preparation of Thiol-Derivatized pBR322 DNA (X=Thiol)

pBR322 plasmid (0.1 mg/ml) was modified with AdoS (Ac) cofactor (10 µM racemate) using HhaIDNA methyltransferase (1 µM) for 1 hour at 37° C. in MOPS pH 7.4 buffer, and then methyltransferase was inactivated by incubating at 80° C. for 20 min. The plasmid was then linearized with the R.EcoRI restriction endonuclease (Fermentas) to yield pBR322-S(Ac) DNA. DNA was extracted with Phenol/Chloroform/isoamyl alcohol mix, and then 2 times with chloroform and applied to DE81 paper filter (Whatman, cat. no. 3658-023), equilibrated with 270 mM NaOAc in a Pierce-SpinCups Paper Filter Column (prod.#69700). The column was washed 2 times with 400 µl of water, and then 200 µl of 25% aqueous ammonia solution was added, column was incubated for 1 hour, washed with 400 µl of water, 200 µl of 0.3 M NaOAc pH 5.0, and 4 times with 400 µl of 0.27 M NaOAc pH 7.0. 200 µl of 50 mM TCEP was added and the column was incubated for 30 min and washed 4 times with 400 µl of 0.27 M NaOAc pH 7.0. The resulting pBR322-SH DNA was eluted with 5 M NaCl and used immediately in step b).

Preparation of Maleimide-Derivatized pBR322 DNA (X=Maleimide)

Alternatively, pBR322 plasmid (0.1 mg/ml) was modified with AdoHxNH2 cofactor (10 µM racemate) using HhaI DNA methyltransferase (1 µM) for 1 hour at 37° C. in MOPS pH 7.4 buffer. The plasmid was then linearized with the R.EcoRI restriction endonuclease (Fermentas) to yield pBR322-NH2 DNA accordingly. DNA was extracted with phenol/chloroform/isoamyl alcohol mix, and then two times with chloroform and applied to DE81 paper filter, equilibrated with 270 mM NaOAc in a Pierce-SpinCups Paper Filter Column. The column was washed 2 times with 0.27 M NaOAc pH 7.0 in 10% DMSO, then 50 µl of 40 mM sulfo-GMBS (N-maleimidobutyryloxy-sulfosuccinimide ester) in DMSO was added and the column was incubated for 1 hour at room temperature. Then column was washed 4 times with 400 µl of 0.27 M NaOAc pH 7.0, the resulting pBR322-N-maleimide DNA was eluted by adding 100 µl of 5 M NaCl, incubating for 5 min and spinning at 1000 rpm for 1 min, and used immediately in step b).

b) Tethering of the Priming Unit to the Site-Specifically Derivatized Plasmid DNA (X-Y Coupling)

Preparation and coupling of maleimide-derivatized oligonucleotide (Y=maleimide) AmT1-maleimide was prepared by combining AmT oligo 100 µM, DMSO 50%, 12.5 mM sulfo-GMBS, 337 mM NaOAc pH 7.0, and incubating for 1 hour at room temperature. Then AmT-maleimide reaction mix-1 solution was diluted with 10 vol water and applied onto a DE81 paper filter (Whatman, cat. no. 3658-023), pre-equilibrated 27 mM NaOAc pH 7.0 in a SpinCup Paper Filter Column (Pierce). Then the column was washed 5 times with 400 µl of NaOAc 27 mM pH 7.0, and AmT-maleimide conjugate was eluted with 3 M NaCl. An equal amount of the pBR322-SH DNA (obtained in step a)) was added and the reaction was incubated overnight under argon atmosphere. Resulting pBR322-S-AmT1 DNA was diluted with water and purified by precipitation with propanol-2, washed with 75% ethanol and redissolved in water.

Preparation and coupling of thiol-derivatized oligonucleotide (Y=thiol) Thiolated OligoM1-EG6-S-S, 5'-ACCTGA-TACTGTACCAGTC-EG6-C3-S-S-C3-3', was reduced with 50 mM TCEP (tris(2-carboxyethyl)phosphine) for two hours, purified by passing through a Illustra MicroSpinG-25 column (GE Healthcare). An equal amount of pBR322 N-maleimide DNA (obtained in step a)) was added and the reaction was incubated overnight at 4° C. under argon atmosphere. Resulting pBR322-oligoM1 DNA was diluted with water and purified by precipitation with propanol-2 washed with 75% ethanol and redissolved in water.

c) Tether-Primed DNA Strand Synthesis in Multiply-Modified Plasmid DNA

Tagged priming and PCR amplification of newly generated strand using locus-specific probes. pBR322-AmT1 and pBR322-oligoM1 fragments were used in Polymerase site-specific priming reaction using probe primers as follows: GGGAGA$_{14}$-Z (Z=A (SEQ ID NO:12), MC (SEQ ID NO:17)) for pBR322-AmT1 template, OligoM2 or OligoM2/OligoM3 oligodeoxyribonucleotides for pBR322-oligoM1 template. OligoM3 is complementary to OligoM2 except for 3 internal nucleotides, and was intended to reduce non-specific binding of OligoM2 to pBR322 template. As a control, unmodified pBR322 plasmid was used as a template. The priming and amplification reaction was performed under the following conditions: template 1 µl from step b), tag-specific primer and locus-specific primer (0.5 µM), Pfu buffer, 2 mM dNTPs in total volume 20 µl, 25 cycles: 95° C./1 min, 58° C./1 min, 72° C./1 min. PCR reactions were analyzed by agarose gel electrophoresis. FIG. 12 demonstrates that all generated PCR fragments are consistent with theoretical predictions based on positions of HhaI sites and the locus primers in the pBR322 sequence.

From the examples described herein, one skilled in the art can easily ascertain the essential principles of this invention and without departing from the spirit and scope thereof, can make various modifications and changes of the invention in adapting to specific uses and conditions.

Applicants incorporate by reference the material contained in the accompanying computer readable Sequence Listing identified as Sequence_Listing_ST25.txt, having a file creation date of Nov. 30, 2012 and file size of 4.92 kilobytes.

What is claimed is:

1. A method for producing a nucleic acid molecule from a template nucleic acid sequence and a linking unit attached to a primer, which method comprises a step of contacting the template nucleic acid sequence with a nucleic acid polymerase under conditions which allow the nucleic acid polymerase to produce the nucleic acid molecule from the primer, wherein the linking unit is attached with a covalent linkage to a target site in the template nucleic acid sequence, wherein the linking unit comprises a primer binding region to which the primer is base paired and a linking region between the primer binding region and the covalent linkage, wherein the linking region does not base pair with the primer or with the nucleic acid molecule that is produced.

2. A method according to claim 1 comprising a step of forming the covalent linkage using a transferase enzyme.

3. A method according to claim 1 wherein the target site is within the template nucleic acid sequence and the linking unit is not attached with the covalent linkage to a terminal nucleotide of the template nucleic acid sequence.

4. A method according to claim 1 wherein the primer comprises no nucleotides that are complementary to the template nucleic acid at the start point of production of the nucleic acid molecule by the nucleic acid polymerase.

5. A method according to claim 1 wherein the primer is also covalently linked to the linking unit.

6. A method according to claim 1 further comprising a step of forming the covalent linkage between the template nucleic acid sequence and the linking unit by contacting the target site derivatized with a first reactive group, with a second reactive group attached to the linking unit, under conditions that allow the first reactive group to react with the second reactive group to form the covalent linkage.

7. A method according to claim 6 further comprising a step of derivatizing the target site with a first reactive group.

8. A method according to claim 7 wherein the step of derivatizing the target site comprises:
  (i) contacting the template nucleic acid sequence with a compound and an enzyme, wherein the compound comprises the first reactive group, and wherein the enzyme is capable of transferring the first reactive group or a part of the compound comprising the first reactive group onto the target site; or
  (ii) contacting the template nucleic acid sequence with a compound, wherein the compound comprises the first reactive group, and the first reactive group or part of the compound comprising the first reactive group is transferred onto the target site through a reaction between the compound and the target site.

9. A method according to claim 8 wherein when the part of the compound comprising the first reactive group is transferred onto the target site, the method further comprises a step of uncovering the first reactive group so that the first reactive group is available for reaction with the second reactive group.

10. A method according to claim 1, further comprising a step of determining the sequence of the produced nucleic acid.

11. A method according to claim 1, further comprising a step of amplifying the produced nucleic acid.

12. A method according to claim 1 wherein the template nucleic acid sequence is DNA or RNA.

13. A method according to claim 1, wherein the target site comprises a nucleotide and the method further comprises, before the step of contacting the template nucleic acid sequence with a nucleic acid polymerase:

(a) derivatizing the nucleotide of the template nucleic acid sequence with a first reactive group by contacting the template nucleic acid sequence with: (i) a target reactive compound comprising the first reactive group; or (ii) a compound comprising a first reactive group and an enzyme, wherein the enzyme is capable of transferring the first reactive group, or a part of the compound comprising the first reactive group, onto the nucleotide;

(b) contacting the nucleic acid sequence with a second reactive group attached to the linking unit under conditions that allow the first reactive group to react with the second reactive group to form a covalent linkage, optionally wherein the linking unit is attached to the primer;

(c) optionally, where the primer is not attached to the linking unit in step (b), binding the primer to the linking unit;

and thereafter detecting the presence or absence of the produced nucleic acid molecule so as to determine the presence or availability of the target site.

14. A method according to claim 13 further comprising sequencing the produced nucleic acid molecule.

15. A method according to claim 13 further comprising a step of PCR amplification of the produced nucleic acid molecule.

16. A method according to claim 13, wherein when in step (a) the part of the compound comprising the first reactive group is transferred onto the nucleotide, the method further comprises a step prior to step (b) of uncovering the first reactive group.

17. A method according to claim 13 wherein the template nucleic acid sequence is an oligonucleotide.

18. A method according to claim 17 further comprising a step of forming the oligonucleotide by mechanical, enzymatic, or chemical digestion of DNA.

19. A method according to claim 18 wherein the step of mechanical digestion is DNA shearing.

20. A method according to claim 13 wherein the covalent linkage is selected from amide, thioureas, imidate, imine, thioether, disulfide, cyclic ester, hydrazone, oxime, thiaxolidine, 1,2,3-triazole, amide, cyclohexene, arylalkyne, biaryl, and diyne.

21. A method according to claim 13 wherein the first reactive group or the second reactive group is an amine, a thiol, a 1,2,-diol, a hydrazine, a hydroxylamine, a 1,2-aminothiol, an azide, a diene, a terminal alkyne, an arylhalide or a terminal silylalkyne, an N-hydroxysuccinimidyl ester, a thioester, an isothiocyanate, an imidoester, an aldehyde, a ketone, a maleimide, a haloacetamide, an aziridine, an arylboronic acid, an alkyne, a phosphane ester, a dienophile, or a terminal haloalkyne.

22. A method according to claim 13 wherein the first reactive group is a terminal alkyne, an amine, a hydroxylamine, a thiol, a maleimide, an alkyne, a hydrazide, an azide, or a carbodiimide.

23. A method according to claim 13 wherein the enzyme is a methyltransferase which is capable of using the compound as a co-factor.

24. A method according to claim 23 wherein the methyltransferase is a DNA methyltransferase or an RNA methyltransferase.

25. A method according to claim 24 wherein the DNA methyltransferase is M.SssI, M.MpeORF4940P, M.HhaI, M.HpaII, M.HsaDnmt1, M.HsaDnmt3A, M.HsaDnmt3B, M.MmuDnmt1, M.MmuDnmt3A, M.MmuDnmt3B, M.HaeIII, M.CviJI, M2.Eco31I, M.EcoRII, M.EcoDcm, M.MvaI, M.BstNI, M.TaqI, M.BseCI, M.Ecodam, T4Dam, M.RsrI or M.EcoRI.

26. A method according to claim 13, wherein the target site comprises an unmethylated cytosine, an unmodified adenine, a 5-hydroxymethylcytosine, or a modified cytosine.

27. A method according to claim 13 wherein the compound is an S-Adenosy-L-methionine analog.

28. A method according to claim 13 wherein the enzyme is a glucosyltransferase.

29. A method according to claim 13 wherein the primer and/or the linking unit further comprise an affinity binding group.

30. A method according to claim 29 further comprising a step of enriching the produced nucleic acid molecules using affinity binding.

31. A template nucleic acid sequence attached to a linking unit and a primer, wherein the linking unit is attached to a target site in the template nucleic acid sequence with a covalent linkage, and wherein the 3' end of the primer is attached to the linking unit.

32. A method according to claim 1 wherein the 3' end of the primer is linked or non-covalently bound to the linking unit.

33. A method according to claim 13 wherein the primer comprises no nucleotides that are complementary to the template nucleic acid at the start point of production of the nucleic acid molecule by the nucleic acid polymerase.

34. A method according to claim 13 wherein step (a) is carried out ex vivo.

35. A method according to claim 13 wherein the template nucleic acid sequence is DNA or RNA.

36. A method according to claim 1, wherein the primer base paired to the nucleotide strand of the linking unit has a recessed 3' end.

* * * * *

SEQUENCE LISTING

<160> NUMBER OF SEQ ID NOS: 21

<210> SEQ ID NO 1
<211> LENGTH: 19
<212> TYPE: DNA
<213> ORGANISM: Artificial Sequence
<220> FEATURE:
<223> OTHER INFORMATION: Tag-specific priming oligodeoxynucleotide

<400> SEQUENCE: 1
gggagaaaaa aaaaaaaaa                                              19

<210> SEQ ID NO 2
<211> LENGTH: 20
<212> TYPE: DNA
<213> ORGANISM: Artificial Sequence
<220> FEATURE:
<223> OTHER INFORMATION: Tag-specific priming oligodeoxynucleotide

<400> SEQUENCE: 2
gggagaaaaa aaaaaaaaaa                                             20

<210> SEQ ID NO 3
<211> LENGTH: 21
<212> TYPE: DNA
<213> ORGANISM: Artificial Sequence
<220> FEATURE:
<223> OTHER INFORMATION: Tag-specific priming oligodeoxynucleotide

<400> SEQUENCE: 3
gggagaaaaa aaaaaaaaaa g                                           21

<210> SEQ ID NO 4
<211> LENGTH: 21
<212> TYPE: DNA
<213> ORGANISM: Artificial Sequence
<220> FEATURE:
<223> OTHER INFORMATION: Tag-specific priming oligodeoxynucleotide

<400> SEQUENCE: 4
gggagaaaaa aaaaaaaaaa c                                           21

<210> SEQ ID NO 5
<211> LENGTH: 23
<212> TYPE: DNA
<213> ORGANISM: Artificial Sequence
<220> FEATURE:
<223> OTHER INFORMATION: Tag-specific priming oligodeoxynucleotide
<220> FEATURE:
<221> NAME/KEY: misc_feature
<222> LOCATION: (21)..(21)
<223> OTHER INFORMATION: n is a, c, g, or t

<400> SEQUENCE: 5
gggagaaaaa aaaaaaaaaa ncg                                         23

<210> SEQ ID NO 6
<211> LENGTH: 21
<212> TYPE: DNA
<213> ORGANISM: Artificial Sequence
<220> FEATURE:
<223> OTHER INFORMATION: Tag-specific priming oligodeoxynucleotide

<400> SEQUENCE: 6
gggagaaaaa aaaaaaaaaa a                                           21

```
<210> SEQ ID NO 7
<211> LENGTH: 22
<212> TYPE: DNA
<213> ORGANISM: Artificial Sequence
<220> FEATURE:
<223> OTHER INFORMATION: Tag-specific priming oligodeoxynucleotide

<400> SEQUENCE: 7
gggagaaaaa aaaaaaaaaa ac                                              22

<210> SEQ ID NO 8
<211> LENGTH: 22
<212> TYPE: DNA
<213> ORGANISM: Artificial Sequence
<220> FEATURE:
<223> OTHER INFORMATION: Tag-specific priming oligodeoxynucleotide
<220> FEATURE:
<221> NAME/KEY: modified_base
<222> LOCATION: (21)..(21)
<223> OTHER INFORMATION: I

<400> SEQUENCE: 8
gggagaaaaa aaaaaaaaaa nc                                              22

<210> SEQ ID NO 9
<211> LENGTH: 19
<212> TYPE: DNA
<213> ORGANISM: Artificial Sequence
<220> FEATURE:
<223> OTHER INFORMATION: Priming adaptor

<400> SEQUENCE: 9
tttttttttt ttttctccc                                                  19

<210> SEQ ID NO 10
<211> LENGTH: 23
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (21)..(21)
<223> OTHER INFORMATION: n is a, c, g, or t

<400> SEQUENCE: 10
gggagaaaaa aaaaaaaaaa ncg                                             23

<210> SEQ ID NO 11
<211> LENGTH: 23
<212> TYPE: DNA
<213> ORGANISM: Artificial Sequence
<220> FEATURE:
<223> OTHER INFORMATION: Oligonucleotide primer
<220> FEATURE:
<221> NAME/KEY: modified_base
<222> LOCATION: (21)..(21)
<223> OTHER INFORMATION: I

<400> SEQUENCE: 11
gggagaaaaa aaaaaaaaaa ngc                                             23

<210> SEQ ID NO 12
<211> LENGTH: 20
<212> TYPE: DNA
<213> ORGANISM: Artificial Sequence
<220> FEATURE:
<223> OTHER INFORMATION: Oligonucleotide primer
```

```
<400> SEQUENCE: 12
gggagaaaaa aaaaaaaaaa                                              20

<210> SEQ ID NO 13
<211> LENGTH: 22
<212> TYPE: DNA
<213> ORGANISM: Artificial Sequence
<220> FEATURE:
<223> OTHER INFORMATION: Oligonucleotide primer
<220> FEATURE:
<221> NAME/KEY: modified_base
<222> LOCATION: (21)..(21)
<223> OTHER INFORMATION: I

<400> SEQUENCE: 13
gggagaaaaa aaaaaaaaaa ng                                           22

<210> SEQ ID NO 14
<211> LENGTH: 22
<212> TYPE: DNA
<213> ORGANISM: Artificial Sequence
<220> FEATURE:
<223> OTHER INFORMATION: Oligonucleotide primer
<220> FEATURE:
<221> NAME/KEY: modified_base
<222> LOCATION: (21)..(21)
<223> OTHER INFORMATION: I

<400> SEQUENCE: 14
gggagaaaaa aaaaaaaaaa nc                                           22

<210> SEQ ID NO 15
<211> LENGTH: 24
<212> TYPE: DNA
<213> ORGANISM: Artificial Sequence
<220> FEATURE:
<223> OTHER INFORMATION: Oligonucleotide primer
<220> FEATURE:
<221> NAME/KEY: modified_base
<222> LOCATION: (22)..(22)
<223> OTHER INFORMATION: I

<400> SEQUENCE: 15
gggagaaaaa aaaaaaaaaa angc                                         24

<210> SEQ ID NO 16
<211> LENGTH: 19
<212> TYPE: DNA
<213> ORGANISM: Artificial Sequence
<220> FEATURE:
<223> OTHER INFORMATION: Thiolated OligoM1-EG6-S-S
<220> FEATURE:
<221> NAME/KEY: misc_feature
<222> LOCATION: (19)..(19)
<223> OTHER INFORMATION: Thiol derivatization

<400> SEQUENCE: 16
acctgatact gtaccagtc                                               19

<210> SEQ ID NO 17
<211> LENGTH: 22
<212> TYPE: DNA
<213> ORGANISM: Artificial Sequence
<220> FEATURE:
<223> OTHER INFORMATION: Probe primer

<400> SEQUENCE: 17
gggagaaaaa aaaaaaaaaa ac                                           22
```

```
<210> SEQ ID NO 18
<211> LENGTH: 10
<212> TYPE: DNA
<213> ORGANISM: Artificial Sequence
<220> FEATURE:
<223> OTHER INFORMATION: Partial sequence - 3' poly A tail

<400> SEQUENCE: 18
aaaaaaaaaa                                                               10

<210> SEQ ID NO 19
<211> LENGTH: 14
<212> TYPE: DNA
<213> ORGANISM: Artificial Sequence
<220> FEATURE:
<223> OTHER INFORMATION: Poly (dT) primer

<400> SEQUENCE: 19
tttttttttt tttt                                                          14

<210> SEQ ID NO 20
<211> LENGTH: 14
<212> TYPE: DNA
<213> ORGANISM: Artificial Sequence
<220> FEATURE:
<223> OTHER INFORMATION: LnkUnit-tethered DNA

<400> SEQUENCE: 20 ttttttttttc tccc                                                         14

<210> SEQ ID NO 21
<211> LENGTH: 21
<212> TYPE: DNA
<213> ORGANISM: Artificial Sequence
<220> FEATURE:
<223> OTHER INFORMATION: Tethered DNA

<400> SEQUENCE: 21
tttttttttt tttttctcc c                                                   21
```